US011786677B2

(12) United States Patent
Sears et al.

(10) Patent No.: US 11,786,677 B2
(45) Date of Patent: Oct. 17, 2023

(54) BRUSHLESS DC MOTOR WITH BEARINGS

(71) Applicant: ResMed Motor Technologies Inc, Chatsworth, CA (US)

(72) Inventors: David B. Sears, Woodland Hills, CA (US); Aleksandr S. Nagorny, Canoga Park, CA (US); Samuel Aziz Mebasser, Chatsworth, CA (US)

(73) Assignee: ResMed Motor Technologies Inc., Chatsworth, CA (US)

( * ) Notice: Subject to any disclaimer, the term of this patent is extended or adjusted under 35 U.S.C. 154(b) by 0 days.

(21) Appl. No.: 17/399,197

(22) Filed: Aug. 11, 2021

(65) Prior Publication Data

US 2021/0369994 A1    Dec. 2, 2021

Related U.S. Application Data

(63) Continuation of application No. 15/908,865, filed on Mar. 1, 2018, now Pat. No. 11,090,453, which is a
(Continued)

(51) Int. Cl.
*H02K 5/128*     (2006.01)
*A61M 16/00*    (2006.01)
(Continued)

(52) U.S. Cl.
CPC ........ *A61M 16/00* (2013.01); *A61M 16/0066* (2013.01); *A61M 16/021* (2017.08);
(Continued)

(58) Field of Classification Search
CPC .... H02K 5/128; H02K 5/1732; H02K 5/1282; H02K 5/1285; H02K 9/197; H02K 7/083;
(Continued)

(56) References Cited

U.S. PATENT DOCUMENTS 2,128,544 A * 8/1938 Surjaninoff ............ H02K 5/128
                                                          310/44
2,661,146 A    12/1953 Hill et al.
(Continued)

FOREIGN PATENT DOCUMENTS

CH     159 238 A    12/1932
CH     269 308       6/1950
(Continued)

OTHER PUBLICATIONS

Communication dated Oct. 20, 2017 issued in European Application No. 16192838.7 (4 pages).
(Continued)

*Primary Examiner* — Michael Andrews
(74) *Attorney, Agent, or Firm* — Nixon & Vanderhye P.C.

(57) ABSTRACT

A brushless DC motor including a rotor, a magnet provided to the rotor, a pair of bearings to rotatably support the rotor, a stator assembly that at least partly surrounds the rotor and magnet thereof and adapted to control movement of the rotor, and a bearing tube having an exterior surface and an interior surface that defines a tube interior. The stator assembly is provided along the exterior surface of the tube and the bearings are provided along the interior surface of the tube to support the rotor and magnet within the tube interior. The motor has sample application for use in PAP devices for delivery of positive airway pressure therapy for users or patients.

25 Claims, 15 Drawing Sheets

Related U.S. Application Data continuation of application No. 14/098,990, filed on Dec. 6, 2013, now Pat. No. 9,937,307, which is a continuation of application No. 12/312,041, filed as application No. PCT/AU2007/022474 on Oct. 24, 2007, now Pat. No. 8,638,014.

(60) Provisional application No. 60/929,558, filed on Jul. 3, 2007, provisional application No. 60/853,778, filed on Oct. 24, 2006.

(51) Int. Cl.
  *H02K 5/173* (2006.01)
  *H02K 7/08* (2006.01)

(52) U.S. Cl.
  CPC ........... *H02K 5/128* (2013.01); *H02K 5/1732* (2013.01); *H02K 7/083* (2013.01); *A61M 2205/42* (2013.01)

(58) Field of Classification Search
  CPC ..... H02K 5/161; H02K 5/1672; A61M 16/00; A61M 16/021; A61M 16/0066; A61M 2205/42
  USPC .................................................. 128/204.18
  See application file for complete search history.

(56) References Cited

U.S. PATENT DOCUMENTS

| | | | |
|---|---|---|---|
| 2,698,911 A | | 1/1955 | Schaefer |
| 2,875,694 A | * | 3/1959 | Carter ................. F04D 13/0633 417/357 |
| 3,138,105 A | * | 6/1964 | White ................. F04D 13/0613 417/357 |
| 3,733,504 A | | 5/1973 | Dennis |
| 4,065,231 A | * | 12/1977 | Litzenberg .......... F04D 13/0613 417/357 |
| 4,161,667 A | | 7/1979 | Buckman et al. |
| 4,533,891 A | | 8/1985 | Vanderlaan et al. |
| 4,655,099 A | | 4/1987 | Hansen |
| 4,883,982 A | | 11/1989 | Forbes et al. |
| 4,930,201 A | * | 6/1990 | Brown ................... H02K 1/278 310/156.28 |
| 4,999,533 A | | 3/1991 | King et al. |
| 5,035,264 A | | 7/1991 | Amico et al. |
| 5,065,061 A | | 11/1991 | Satoh et al. |
| 5,168,186 A | * | 12/1992 | Yashiro ................. H02K 5/128 310/156.28 |
| 5,325,059 A | | 6/1994 | Doty |
| 5,463,490 A | * | 10/1995 | Seto ..................... G02B 26/121 310/90 |
| 5,567,127 A | | 10/1996 | Wentz |
| 5,844,338 A | | 12/1998 | Horski |
| 5,949,171 A | | 9/1999 | Horski |
| 6,076,795 A | | 6/2000 | Scheidel et al. |
| 6,081,050 A | | 6/2000 | Hong et al. |
| 6,216,691 B1 | | 4/2001 | Kenyon et al. |
| 6,309,180 B1 | * | 10/2001 | Gilliland ................... H02K 9/06 415/208.2 |
| 6,315,526 B1 | | 11/2001 | Jones |
| 6,349,724 B1 | | 2/2002 | Burton et al. |
| 6,439,861 B1 | | 8/2002 | Shieh |
| 6,717,299 B2 | | 4/2004 | Bacile et al. |
| 6,910,483 B2 | | 6/2005 | Daly et al. |
| 6,919,659 B2 | | 7/2005 | Rapp |
| 7,019,423 B1 | | 3/2006 | Horing et al. |
| 7,058,291 B2 | | 6/2006 | Weaver et al. |
| 8,638,014 B2 | | 1/2014 | Sears et al. |
| 9,937,307 B2 | | 4/2018 | Sears et al. |
| 2001/0033742 A1 | | 10/2001 | Weaver et al. |
| 2002/0057967 A1 | | 5/2002 | Eimer et al. |
| 2003/0080635 A1 | | 5/2003 | Bacile |
| 2003/0146670 A1 | * | 8/2003 | Van Dine ............. H02K 5/1285 310/85 |
| 2003/0178903 A1 | * | 9/2003 | Rapp ..................... H02K 5/128 310/90 |
| 2003/0188397 A1 | | 10/2003 | Syverson et al. |
| 2005/0036887 A1 | | 2/2005 | Nadjafizadeh et al. |
| 2005/0074346 A1 | | 4/2005 | Hoyt et al. |
| 2005/0095151 A1 | | 5/2005 | Wampler et al. |
| 2005/0103339 A1 | | 5/2005 | Daly et al. |
| 2005/0123424 A1 | | 6/2005 | Wickham et al. |
| 2005/0210622 A1 | | 9/2005 | Baecke |
| 2005/0247315 A1 | | 11/2005 | Estes et al. |
| 2006/0181168 A1 | | 8/2006 | Hargraves et al. |
| 2008/0304986 A1 | | 12/2008 | Kenyon |
| 2010/0059056 A1 | | 3/2010 | Sears et al. |
| 2014/0090645 A1 | | 4/2014 | Sears et al. |
| 2014/0101926 A1 | | 4/2014 | Kenyon et al. |
| 2018/0185594 A1 | | 7/2018 | Sears et al. |

FOREIGN PATENT DOCUMENTS

| | | |
|---|---|---|
| CH | 269308 A | 6/1950 |
| DE | 196 28 118 | 1/1998 |
| DE | 103 20 703 | 12/2004 |
| EP | 0 232 834 | 8/1987 |
| EP | 0 531 588 | 3/1993 |
| EP | 0 963 029 | 12/1999 |
| EP | 1 037 365 | 9/2000 |
| EP | 1 376 822 | 1/2004 |
| EP | 1 580 434 A1 | 9/2005 |
| EP | 1 318 307 | 6/2006 |
| EP | 2 000 675 A | 12/2008 |
| GB | 1029177 | 5/1966 |
| GB | 1 186 381 | 4/1970 |
| GB | 1 467 164 | 3/1977 |
| GB | 2 260 861 | 4/1993 |
| JP | S61-185248 | 11/1986 |
| JP | S62-185528 | 8/1987 |
| JP | H03-007671 | 1/1991 |
| JP | H04-033550 | 2/1992 |
| JP | H05-111216 | 4/1993 |
| JP | 2826172 | 11/1998 |
| JP | 2000-509959 | 8/2000 |
| JP | 3086019 | 3/2002 |
| JP | 2002-227792 | 8/2002 |
| JP | 2004-500969 | 1/2004 |
| JP | 2004-312821 | 11/2004 |
| JP | 2005-245139 | 9/2005 |
| JP | 2005-299617 | 10/2005 |
| KR | 10-2003-0019477 | 3/2003 |
| WO | WO 94/17306 | 8/1994 |
| WO | 96/04043 A1 | 2/1996 |
| WO | WO 02/007290 | 1/2002 |
| WO | WO 2004/057729 | 7/2004 |
| WO | WO 2004/092582 | 10/2004 |
| WO | WO 2004/108198 | 12/2004 |
| WO | PCT/AU2006/001617 | 10/2006 |

OTHER PUBLICATIONS

First Examination Report dated Apr. 5, 2017 issued in New Zealand Application No. 729644 (3 pages).
Decision of Commissioner dated Apr. 5, 2017 issued in New Zealand Application No. 603342 (1 page).
Decision of Assistant Commissioner of Patents dated Apr. 5, 2017 issued in New Zealand Application No. 603342 (20 pages).
Extended Search Report dated Feb. 6, 2017 issued in European Application No. 16192838.7 (7 pages).
Communication pursuant to Article 94(3) EPC issued in corresponding European Application No. 07 861 481.5 dated May 18, 2016.
Second Amended Counterstatement—in marked-up and clean formats filed by Applicant on Feb. 16, 2016 in corresponding New Zealand Application No. 603342,.
Proceeding Correspondence issued in corresponding New Zealand Application No. 603342 dated Feb. 26, 2016.

(56) References Cited

OTHER PUBLICATIONS

Affirmation of Nicola Jane Kahn filed by Fisher and Paykel Healthcare Limited on Feb. 29, 2016 in corresponding New Zealand Application No. 603342.
Cover Sheet Letter for Second Amended Statement of Case filed Fisher & Paykel Healthcare Limited in corresponding New Zealand Application No. 603342 on Dec. 17, 2015,.
Second Amended Statement of Case—in marked-up and clean formats filed by Fisher & Paykel Healthcare Limited in corresponding New Zealand Application No. 603342 on Dec. 17, 2015.
Third Amended Notice of Opposition to Grant of Patent (Section 21)—in marked-up and clean formats filed by Fisher & Paykel Healthcare Limited in corresponding New Zealand Application No. 603342 on Dec. 17, 2015.
Patent Examination Report No. 2 issued in corresponding Australian Application No. 2013222004 dated Dec. 3, 2015.
First Examination Report issued in corresponding New Zealand Application No. 710974 dated Sep. 11, 2015.
Communication pursuant to Article 94(3) EPC issued in corresponding European Application No. 07 861 481.5 dated Sep. 18, 2015.
Notice of Allowance issued in corresponding Korean Application No. 2013-7033294 dated Sep. 24, 2015, with English translation thereof.
Office Action issued in corresponding Korean Application No. 10-2013-7033294 dated Jul. 21, 2015, with English translation thereof.
Further Examination Report issued in corresponding New Zealand Application No. 619994 dated Jun. 16, 2015.
Patent Examination Report issued in corresponding Australian Appln. No. 2013222004 dated Mar. 25, 2015.
Proceeding Correspondence issued in corresponding New Zealand Application No. 603342 dated Jun. 24, 2015.
Second Amended Notice of Opposition to Grant Patent (Section 21)—in marked-up and clean formats filed by Fisher & Paykel Healthcare Limited in corresponding New Zealand Patent Application No. 603342 on Jun. 24, 2015.
Amended Statement of Case—in marked-up and clean formats filed by Fisher & Paykel Healthcare Limited in corresponding New Zealand Application No. 603342 on Jun. 24, 2015.
Third Office Action issued in corresponding Chinese Appln. No. 201210345608.9 dated Apr. 28, 2015, with English translation thereof.
Decision of Final Rejection issued in corresponding Korean Appln. No. 10-2013-7033294 dated Apr. 27, 2015, with English translation thereof.
U.S. Appl. No. 60/730,875, filed Oct. 2005, Kenyon et al.
U.S. Appl. No. 60/775,333, filed Feb. 2006, Kenyon et al.
U.S. Appl. No. 60/877,373, filed Dec. 2006, Suzuki et al.
Communication issued in European Appln. No. 07 861 481.5 dated Jan. 27, 2015 (4 pages).
Notice of Opposition to Grant of Patent filed by Fisher & Paykel Healthcare Limited in New Zealand Patent Application No. 603342 on Dec. 22, 2014 (2 pages).
Extension of Time Granted issued in corresponding Application No. 603342 dated Jan. 5, 2015 (1 page).
Statement of Case and Amended Notice of Opposition to Grant of Patent filed by Fisher & Paykel Healthcare Limited in New Zealand Application No. 603342 on Mar. 2, 2015 (10 pages).

Chinese Office Action issued in corresponding Appln. No. 201210345608.9 dated Dec. 25, 2014, with English language translation thereof.
Korean Decision of Final Rejection issued in corresponding Appln. No. 2014-7014799 dated Jan. 9, 2015, with English language translation thereof.
Office Action issued in corresponding Korean Appln. No. 10-2013-7033294 dated Oct. 8, 2014, with English language translation thereof.
Office Action issued in corresponding Korean Appln. No. 10-2014-7014799 dated Jul. 9, 2014, with English language translation thereof.
Office Action issued in a corresponding Japanese Appln. No. 2013-078856 dated Mar. 10, 2014, with English language translation thereof.
Office Action issued in a corresponding Korean Appln. No. 10-2009-7010534 dated Mar. 11, 2014, with English language translation thereof.
Office Action issued in a corresponding Korean Appln. No. 10-2013-7033294 dated Mar. 7, 2014, with English language translation thereof.
Communication issued in a corresponding European Appln. No. 07 861 481.5 dated Jan. 16, 2014.
Further Examination Report issued in a corresponding New Zealand Appln. No. 603342 dated Feb. 12, 2014.
First Examination Report issued in a corresponding New Zealand Appln. No. 619994 dated Feb. 14, 2014.
Office Action issued in corresponding Chinese Appln. No. 201210345608.9 dated May 5, 2014, with English translation thereof.
International Search Report for PCT/AU2007/022474, dated Mar. 7, 2008.
First Office Action issued in a Chinese Appln. No. 200780039629.5 (dated Oct. 29, 2010) with English translation.
Search and Examination Report issued in a Singapore Appln. No. 200902510-7 (dated Oct. 8, 2010).
Examination Report issued in a New Zealand Appln. No. 576965 (dated Nov. 5, 2010).
Examination Report issued in a related Australian Appln. No. 200709509 (dated Dec. 16, 2011).
Examination Report issued in a related NZ Appln. No. 596357 (dated Nov. 18, 2011).
Second Office Action issued in a related Chinese Appln. No. 200780039629.5 (dated Jan. 18, 2012).
Examiner's Report issued in a related Australian Appln. No. 2007309509 (dated Dec. 16, 2011).
Office Action issued in a corresponding Japanese Appl. No. 2009-534625 (dated Dec. 4, 2012) with English translation thereof.
Examination Report issued in a corresponding New Zealand Appl. No. 596357 (dated Nov. 7, 2012).
Examination Report issued in a corresponding New Zealand Appl. No. 603342 (dated Nov. 7, 2012).
Extended EP Search Report dated Dec. 14, 2012 issued in EP Application No. 07861481.5.
Patent Examination Report No. 2 issued in a corresponding Appl. No. 2007309509 dated Jan. 24, 2013.
Patent Examination Report No. 3 issued in a corresponding Australian Appl. No. 2007309509 dated Mar. 19, 2013.
Office Action issued in a corresponding Korean Application No. 10-2009-7010534, dated Oct. 14, 2013 with English language translation thereof.

\* cited by examiner

BRUSHLESS DC MOTOR WITH BEARINGS

CROSS-REFERENCE TO RELATED APPLICATIONS

This application is a continuation of U.S. patent application Ser. No. 15/908,865, filed Mar. 1, 2018, which is a continuation of U.S. patent application Ser. No. 14/098,990, filed Dec. 6, 2013, now U.S. Pat. No. 9,937,307, which is a continuation of U.S. patent application Ser. No. 12/312,041, filed Apr. 23, 2009, now U.S. Pat. No. 8,638,014, which is the U.S. National Phase of International Application No. PCT/US2007/022474, filed Oct. 24, 2007, which designated the U.S. and claims the benefit of U.S. Provisional Application Nos. 60/853,778, filed Oct. 24, 2006, and 60/929,558, filed Jul. 3, 2007, each of which is incorporated herein by reference in its entirety.

FIELD OF THE INVENTION

The present invention relates to electric motors, and more particularly to bearing supported rotors of the electric motor. The present invention also relates to electric motors for positive airway pressure (PAP) devices or flow generators used for treatment, e.g., of Sleep Disordered Breathing (SDB) with Non-Invasive Positive Pressure Ventilation (NIPPV).

BACKGROUND OF THE INVENTION

Bearings are usually employed in pairs and in coaxial arrangements to support a rotating member, e.g., motor shaft. Ideally, the two bearings are located by a stationary member that constrains the two bearings in perfect axial alignment. Real world designs are less than perfect and, therefore, compromise bearing performance.

A widely employed bearing suspension mode involves holding each bearing within a separate housing structure and fitting those housing structures together to approximate a coaxial bearing arrangement. For example, FIG. 7 illustrates a housing H holding bearing B1 and a cap C holding bearing B2, the cap C being fitted to the housing H to support a rotor R between the bearings B1, B2.

There are two main classes of constraints on the packaging of bearings. One constraint relates to the practical limits of manufacturing precision, and another constraint relates to the need to attach and efficiently package items that must rotate.

With respect to the first constraint, although the precision of part forming technologies improves continuously, the state of the art is far from perfect. Furthermore, increased precision usually translates to greater expense, often dissuading a manufacturer from embracing the state of the art processes.

The second constraint is driven by the need to place items (such as a rotor/stator) between bearing pairs. This leads to the use of a two part housing construction. A consequence of multipart housings is that they accumulate unwanted tolerance build-up at each faying or joint surface.

A less widely employed bearing suspension mode is to utilize a single metallic tube to house the bearing pair, and to hang the rotor from one end in cantilever fashion, i.e., an outer rotor design. For example, FIG. 8 illustrates a metallic tube T housing bearings B1, B2, and a rotor R supported by the bearings B1, B2 in cantilever fashion to support an impeller I. However, the metallic tube prevents a high speed magnetic rotor from being packaged between the bearings, i.e., an internal rotor design, because magnetic fields cannot effectively cross a metallic barrier without significant loss of flux density and/or increased heat. Also, there are practical limits to how much mass and length can be cantilevered from a set of high speed bearings. Therefore, such designs tend to be axially short in length.

Thus, a need has developed in the art for an improved arrangement that does not suffer from the above-mentioned drawbacks.

SUMMARY OF THE INVENTION

One aspect of the invention relates to a rotor supporting structure to support a rotor in use.

Another aspect of the invention relates to a bearing arrangement having at least two bearing portions supported on a common member, e.g., bearing tube.

Another aspect of the invention relates to a brushless DC motor with bearings retained in a stationary tube having at least a portion that is sufficiently magnetically transparent to allow a magnetic field to pass through it, e.g., non-electrically conductive and/or non-magnetic tube. In the context of an embodiment of the invention, a non-conductive material may be a material with relatively high resistivity (for example, in the vicinity of 2 micro Ohm-m or more) and a non-magnetic material may be a material with relatively low magnetic permeability (for example, in the vicinity of 2 or less). The acceptable ranges of these material characteristics may vary from case to case. The tube may be generally thermally conductive, and such tube can be metallic and/or non-metallic or semi-metallic.

Another aspect of the invention relates to a brushless DC motor including a rotor, a magnet provided to the rotor, a pair of bearings to rotatably support the rotor, a stator assembly that at least partly surrounds the rotor and magnet thereof, and a bearing tube having an exterior surface and an interior surface that defines a tube interior. The stator assembly is adapted to control movement of the rotor. The stator assembly is provided along the exterior surface of the tube and the bearings are provided along the interior surface of the tube to support the rotor and magnet within the tube interior. The tube has at least a portion that is sufficiently magnetically transparent to allow a magnetic field to pass between the magnet and the stator assembly.

Another aspect of the invention relates to a brushless DC motor including a rotor having a magnet, a stator assembly adapted to control movement of the rotor, and a tube provided between the rotor and the stator assembly. The tube has at least a portion that is sufficiently magnetically transparent to allow a magnetic field to pass between the magnet and the stator assembly.

Another aspect of the invention relates to a brushless DC motor including a magnetic rotor rotatably supported between a pair of bearings, a stator assembly surrounding the rotor and adapted to control movement of the rotor, and a tube to retain the bearings and rotor within an interior of the tube. The tube has at least a portion that is sufficiently magnetically transparent to allow a magnetic field to pass between the magnetic rotor and the stator assembly.

Another aspect of the invention relates to a PAP device for generating a supply of pressurized gas to be provided to a patient for treatment. The PAP device includes a housing, a core including a motor and at least one impeller, and a vibration isolation system to support the core within the housing in a flexible, vibration-isolated manner.

Another aspect of the invention relates to a PAP device for generating a supply of pressurized gas to be provided to a patient for treatment. The PAP device includes a housing, a core including a motor and at least one impeller, and a vibration isolation system to support the core within the housing in a flexible, vibration-isolated manner. The vibration isolation system is adapted to be coupled to windings of a stator assembly to conduct current from an external source to the windings.

Another aspect of the invention relates to a brushless DC motor including a rotor, a stator assembly surrounding the rotor and adapted to control movement of the rotor, a support structure to support the rotor and the stator assembly in an operative position, and a vibration isolation system provided to the support structure and adapted to support the support structure within a housing in a flexible, vibration-isolated manner.

Another aspect of the invention relates to a method for manufacturing a motor. The method includes forming a tube having at least a portion that is sufficiently magnetically transparent to allow a magnetic field to pass through it, providing a magnetic rotor to an interior portion of the tube, and providing a stator assembly to an exterior portion of the tube to control movement of the magnetic rotor.

Another aspect of the invention relates to a rotor supporting structure including at least one bearing support portion adapted to support a bearing and a sufficiently magnetically transparent portion to allow a magnetic field to pass through it.

Other aspects, features, and advantages of this invention will become apparent from the following detailed description when taken in conjunction with the accompanying drawings, which are a part of this disclosure and which illustrate, by way of example, principles of the invention.

BRIEF DESCRIPTION OF THE DRAWINGS

The accompanying drawings facilitate an understanding of the various embodiments of this invention. In such drawings:

FIG. 3-1 is a perspective view of a rotor, tube, and stator assembly for an electric motor according to another embodiment of the present invention;

FIG. 3-2 is a cross-sectional view of the assembly of the electric motor shown in FIG. 3-1;

FIG. 4-1 is a perspective, cross-sectional view of a PAP device according to another embodiment of the present invention;

FIG. 4-2 is a top view of the PAP device shown in FIG. 4-1;

FIG. 4-3 is another cross-sectional view of the PAP device shown in FIG. 4-1;

FIG. 5-1 is a perspective, cross-sectional view of a PAP device according to another embodiment of the present invention;

FIG. 5-2 is another cross-sectional view of the PAP device shown in FIG. 5-1;

FIG. 5-3 is an enlarged cross-sectional view of a portion of the PAP device shown in FIG. 5-1;

FIG. 5-4 is a side view of the PAP device shown in FIG. 5-1;

FIG. 5-5 is a perspective view of a core of the PAP device shown in FIG. 5-1;

FIG. 5-6 is a cross-sectional view of the core shown in FIG. 5-5;

FIG. 6 is a cross-section view illustrating a method for assembling bearings according to an embodiment of the present invention;

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the PAP devices described herein may be designed to pump fluids or gases other than air.

1. Electric Motor

Figure 1:
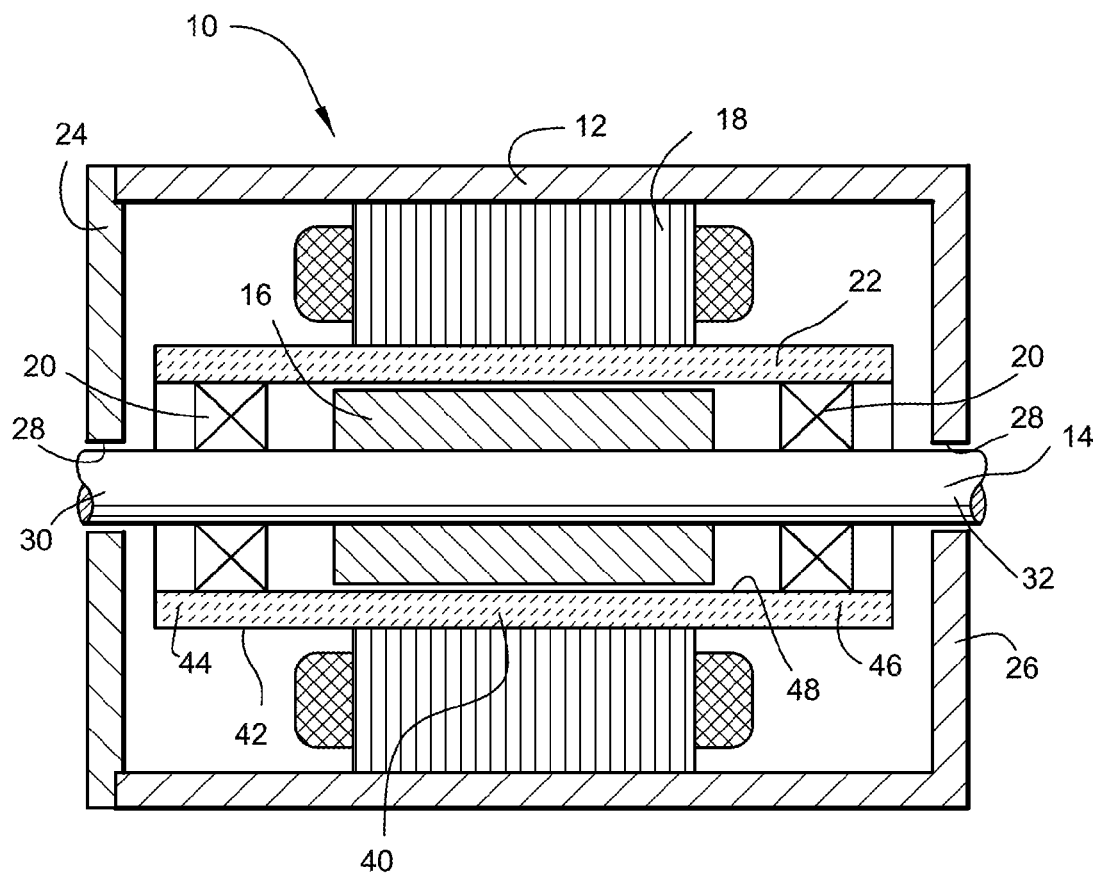
FIG. 1 is a partial cross-sectional view of an electric motor including a bearing tube according to an embodiment of the present invention.

FIG. 1 illustrates an electric motor or tube motor 10 according to an embodiment of the present invention. In the illustrated embodiment, the motor 10 is in the form of a brushless DC motor. The motor 10 includes an optional housing 12, a rotatable shaft or rotor 14, a permanent magnet 16 mounted on the rotor 14, and a stator assembly 18 that surrounds the rotor 14 and magnet 16 thereof. The rotor 14 is rotatably supported by a pair of bearings 20 that are retained or housed by a bearing tube 22. The bearings 20 may be any suitable type as known in the art, e.g., conventional rolling element bearings, fluid bearings (air or liquid), sleeve bearings, or other type.

The optional housing 12 encloses the stator assembly 18, rotor 14, magnet 16, bearings 20, and bearing tube 22. An end cap 24 is provided to the housing 12 to allow access to the housing interior and the components enclosed therein. In addition, the end cap 24 and end wall 26 of the housing each include an opening 28 to allow respective end portions 30, 32 of the rotor 14 to extend therethrough. Each end portion 30, 32 is adapted to be coupled to a device, e.g., impeller, to cause spinning movement of the device. However, the motor 10 may be structured such that only one end portion of the rotor 14 extends from the housing 12. In use, an electronic controller (typically provided as part of PAP devices or flow generators available from ResMed) controls operation of the stator assembly 18 to control spinning movement of the rotor 14 and hence the device, e.g., impeller.

1.1 Bearing Tube

In the illustrated embodiment, the bearing tube 22 comprises a relatively thin-walled, stationary, stable tube.

1.1.1 Properties

The bearing tube 22 has at least a portion that is sufficiently magnetically transparent to allow a magnetic field to pass through it. In an embodiment, such "magnetic transparency" may be provided by one or more the tube's material properties, e.g., non-electrically conductive, magnetically transparent or non-magnetic, and/or thermally conductive tube. Alternatively, such "magnetic transparency" may be provided by one or more perforations in the tube as described in greater detail below.

In some applications, it may not be necessary for the tube to have all the material properties described above (non-electrically conductive, magnetically transparent, and thermally conductive) as the tube may simply include one or more of these properties and/or a sufficient degree of these properties (e.g., partially electrically conductive and/or partially heat conductive). In addition, non-conductive refers to the (non)conduction of electricity, although the tube 22 may be heat conductive in embodiments, which may be beneficial for warming the air and/or cooling the blower elements. The tube includes adequate "magnetic transparency", "non-electrical conductivity", and/or "thermal conductivity" to allow sufficient magnetic flux near the magnet without overheating.

In the context of an embodiment of the invention, a non-conductive material is understood to be a material with relatively high resistivity (for example, in the vicinity of 2 micro Ohm-m or more) and a non-magnetic material is understood to be a material with relatively low magnetic permeability (for example, in the vicinity of 2 or less). The acceptable ranges of these material characteristics may vary, e.g., depending on application.

The tube may be thermally conductive to allow heat release (heat may create drag on motor, inefficient power, reduced life on bearings, tube distortion, etc.).

In addition, the tube may have different material properties along its length or circumference, e.g., different levels or regions of "magnetic transparency", "non-electrical conductivity", and/or "thermal conductivity." That is, portions of the tube may have one or more of these properties, but other portions of the tube may not.

Magnetic transparency should be greater in the vicinity of the magnet and stator assembly, where flux densities may be expected to be higher. Outside of that region, different properties could be tolerated and in some cases may not be necessary. For example, it could be advantageous to construct the tube from different elements that are fastened together, wherein some of the elements are magnetically transparent, in locations where that is desirable, and other elements of the tube are more thermally conductive, for example.

1.1.2 Materials

The bearing tube 22 may be constructed of non-metallic materials, e.g., ceramics (e.g., stabilized zirconia), glass, polymers, filled (but non-conductive) polymers, or reinforced polymers (e.g., Fiberglass, Carbon, Boron, etc.). However, the tube can also be metallic or semi-metallic. In an embodiment, the tube may include different materials along its length or circumference.

1.1.3 Shapes

In the illustrated embodiment, the tube has a circular cross-sectional configuration along its length. However, it should be appreciated that the tube may have other suitable shapes, e.g., circular or round, square, polygonal, conical, etc.

Also, the tube may include one or more parts (e.g., multi-part construction), e.g., different elements with different properties that are fastened together.

In an embodiment, the tube may be sufficiently perforated (e.g., one or more holes, openings, and/or slits) to allow a magnetic field to pass through it. In such embodiment, the tube may or may not include non-electrically conductive, magnetically transparent, and/or thermally conductive material properties.

1.1.4 Combinations

It is to be understood that any single feature or combination of features described above may constitute embodiments of the tube. That is, the tube may include any suitable combination of properties, materials, and/or shapes as described above.

1.1.5 Portions

Also, it should be understood that portions of the tube may have one or more of the features described above, but other portions of the tube may not.

1.1.6 Bearing Support

As illustrated, the stator assembly 18 is provided to a center portion 40 of the tube 22 along an exterior surface 42 thereof. The bearings 20 are provided to respective end portions 44, 46 of the tube 22 along an interior surface 48 thereof. The tube 22 retains the bearings 20 in substantially perfect axial alignment. The bearings 20 support the rotor 14 and magnet 16 within the tube interior. In addition, the magnet 16 is positioned between the bearings 20 such that the magnet 16 is aligned with the stator assembly 18.

The inside diameter of the tube 22 is substantially similar to the outside diameter of the bearings 20. This allows the bearings 20 to be securely and stably retained within the tube 22, e.g., by friction fit, adhesive, etc.

The tube 22 is sufficiently "magnetically transparent" (e.g., non-magnetic, non-electrically conductive, and/or thermally conductive), which allows the motor 10 to have a design in which the magnetic rotor 14 is located between the bearings 20 within the tube 22, as illustrated in FIG. 1. That is, the stator assembly 18 can act on the magnetic rotor 14 positioned within the tube 22 without significant loss of flux density and/or increased heat, if any. Thus, the tube 22 provides stable physical properties and is adequate to support the needs of the motor application. It is noted that the bearing tube 22 may be incorporated into other motor arrangements or other applications where "magnetic transparency" may be beneficial.

1.2 Advantages

The motor arrangement of FIG. 1, in which the magnetic rotor 14 is positioned within the "magnetically transparent" tube, 22 has several advantages. For example, the motor arrangement provides superior bearing-to-bearing alignment. The superior alignment results in improved noise and/or improved life. In addition, the superior alignment results in the ability to better accommodate fluid bearings, e.g., when the materials of the rotor and the tube have closely matched thermal expansion coefficients (e.g., both the tube and rotor may be made of stabilized zirconia).

The motor arrangement also provides superior compactness (e.g., the rotor may reside between the tube mounted bearings, not cantilevered), superior dynamic response due to an inherently low inertia rotor, and superior rigidity due to simplicity of construction. In addition, the motor arrangement provides superior accommodation of both fluid bearings and a double-ended, impeller blower construction (e.g., when the motor is incorporated into a PAP device or flow generator as described below).

Further, when rolling element bearings are used, matched thermal coefficients of the tube and rotor may allow one to eliminate a preload spring. Specifically, one method for assembling bearings includes using a preload spring that applies a force to the bearings to ensure they remain correctly aligned and retained in position against the ends of tube, e.g., against flange 380 for the lower bearing and against tapered flange 382 for the upper bearing as shown FIG. 4-3. As an alternative to such method, the preload spring may be eliminated and the bearings may be retained in position by an adhesive, e.g., glue, or other suitable fixing means, e.g., mechanical fasteners, etc. The bearings may be of a range of varieties. For example, the bearings could be constructed as sleeve types, duplex types, magnetic types, etc.

Figures 1, 5:
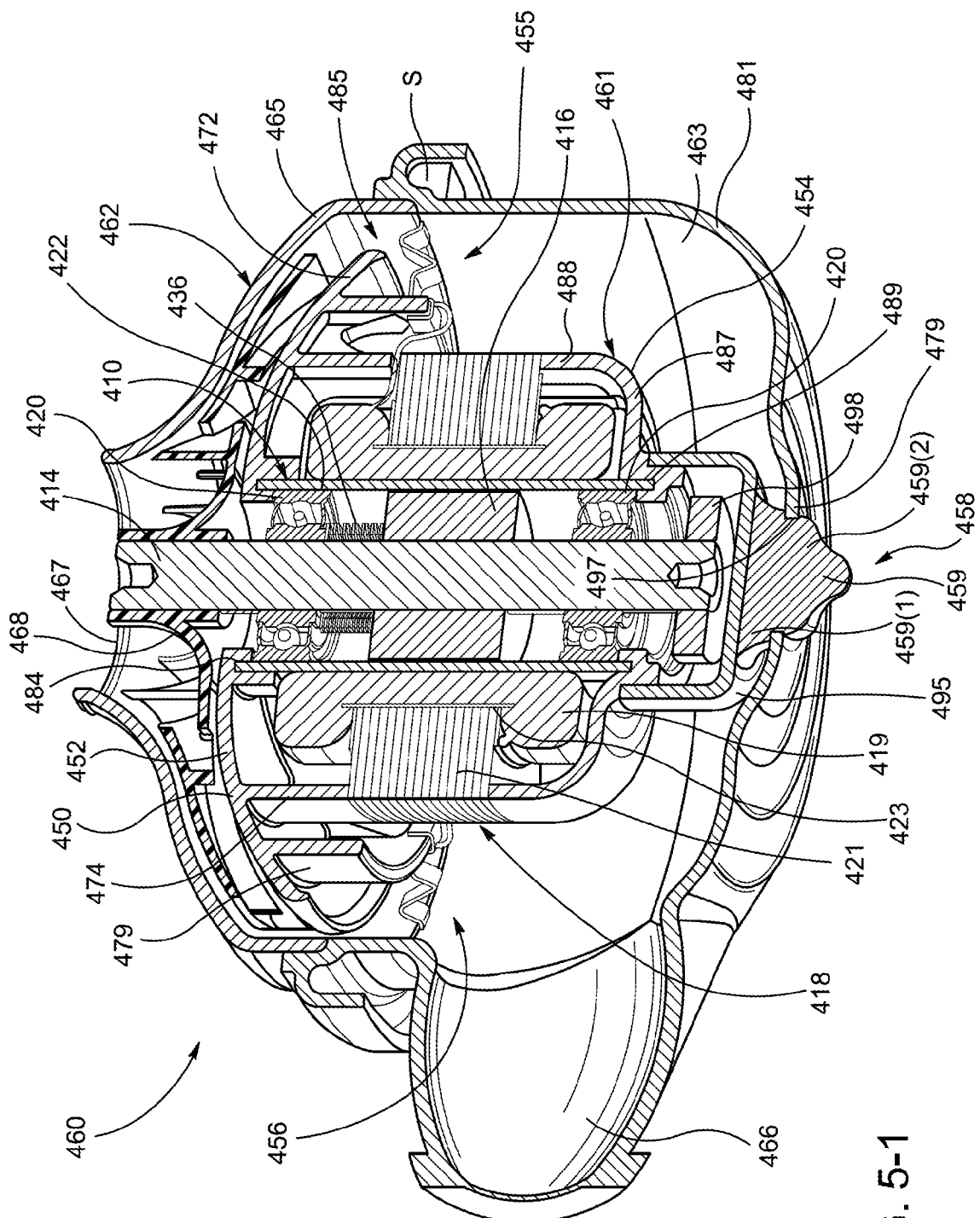
Figures 2, 5:
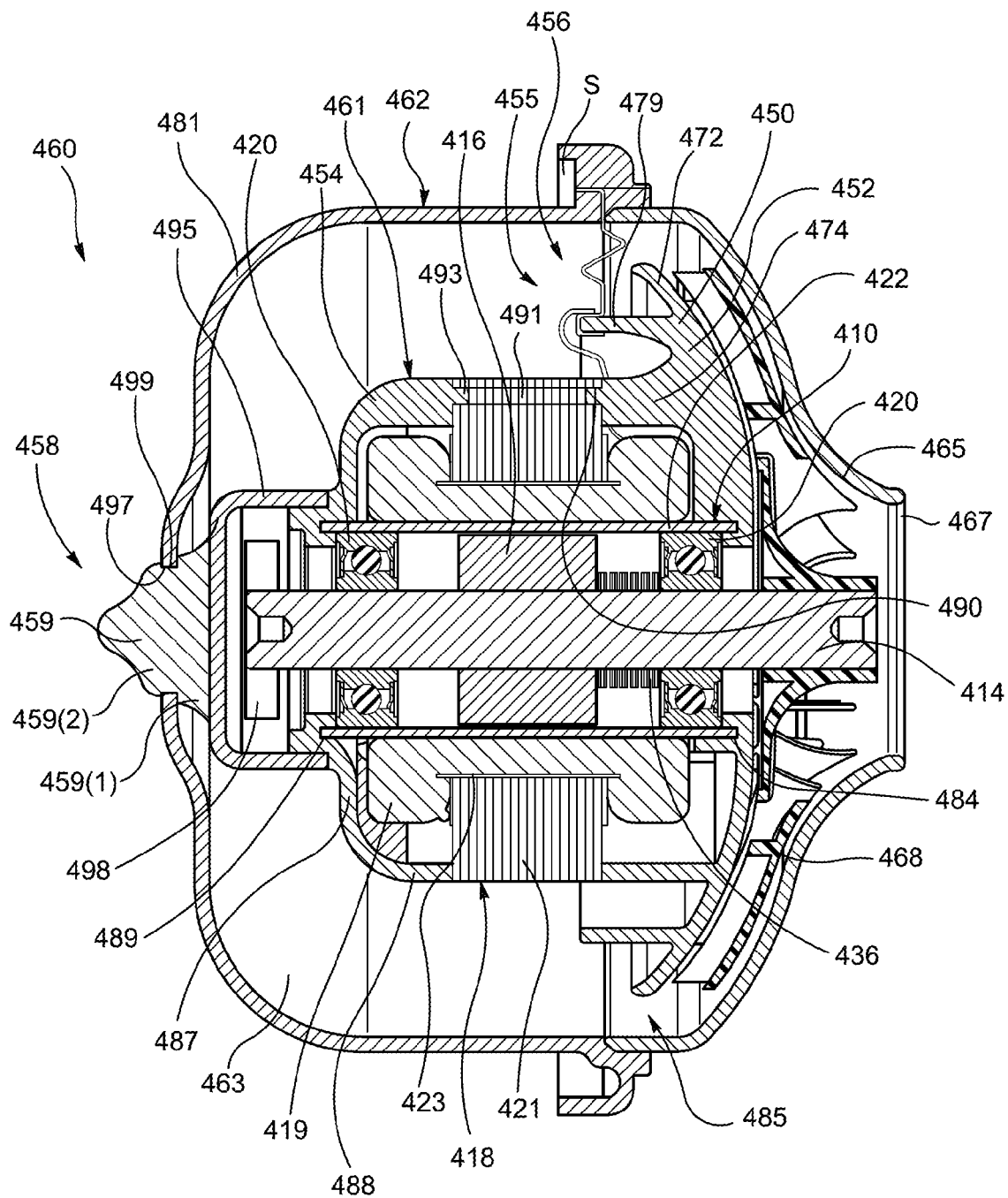
Figures 3, 5:
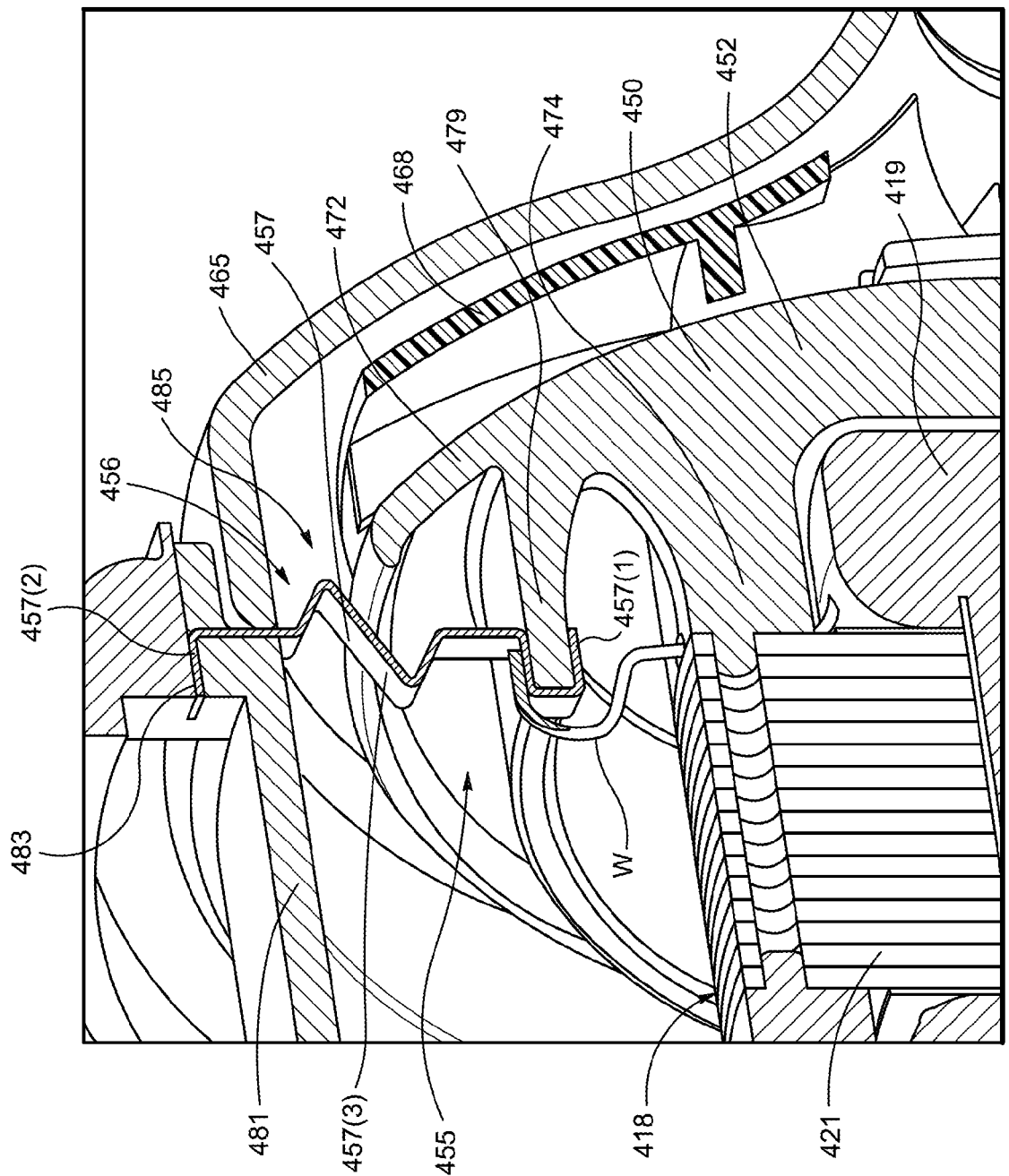
Figures 4, 5:
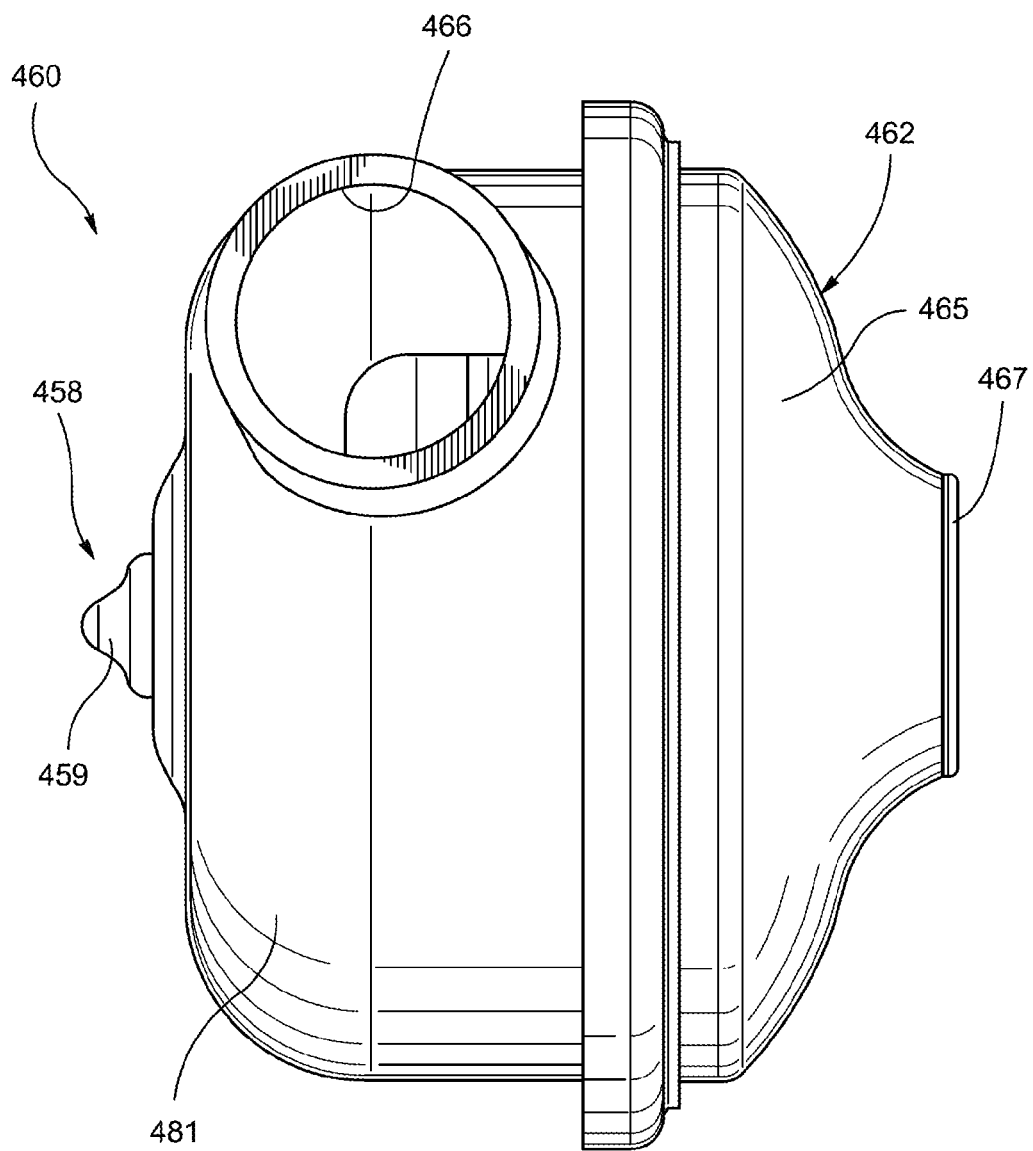
Figure 5:
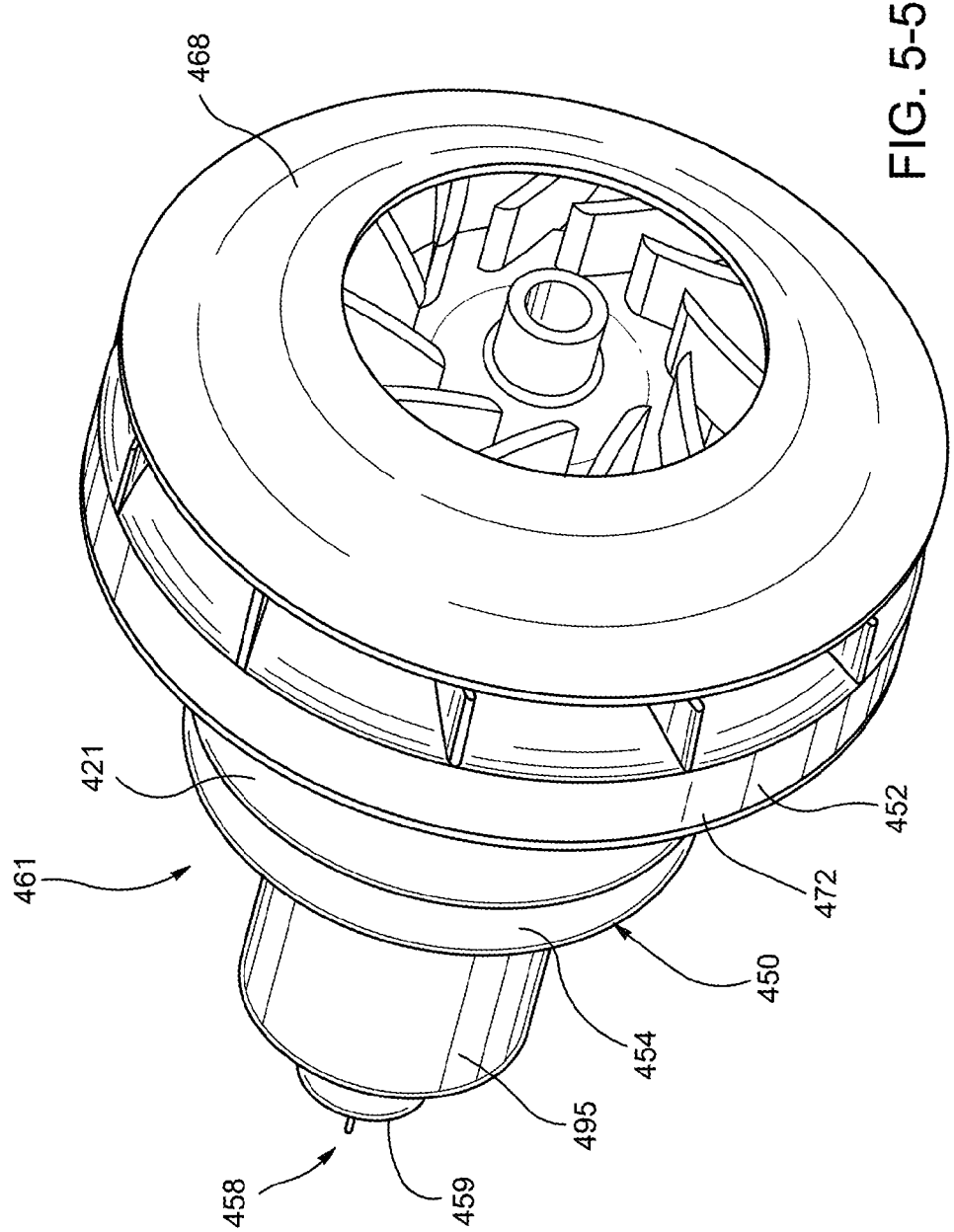
Figures 5, 6:
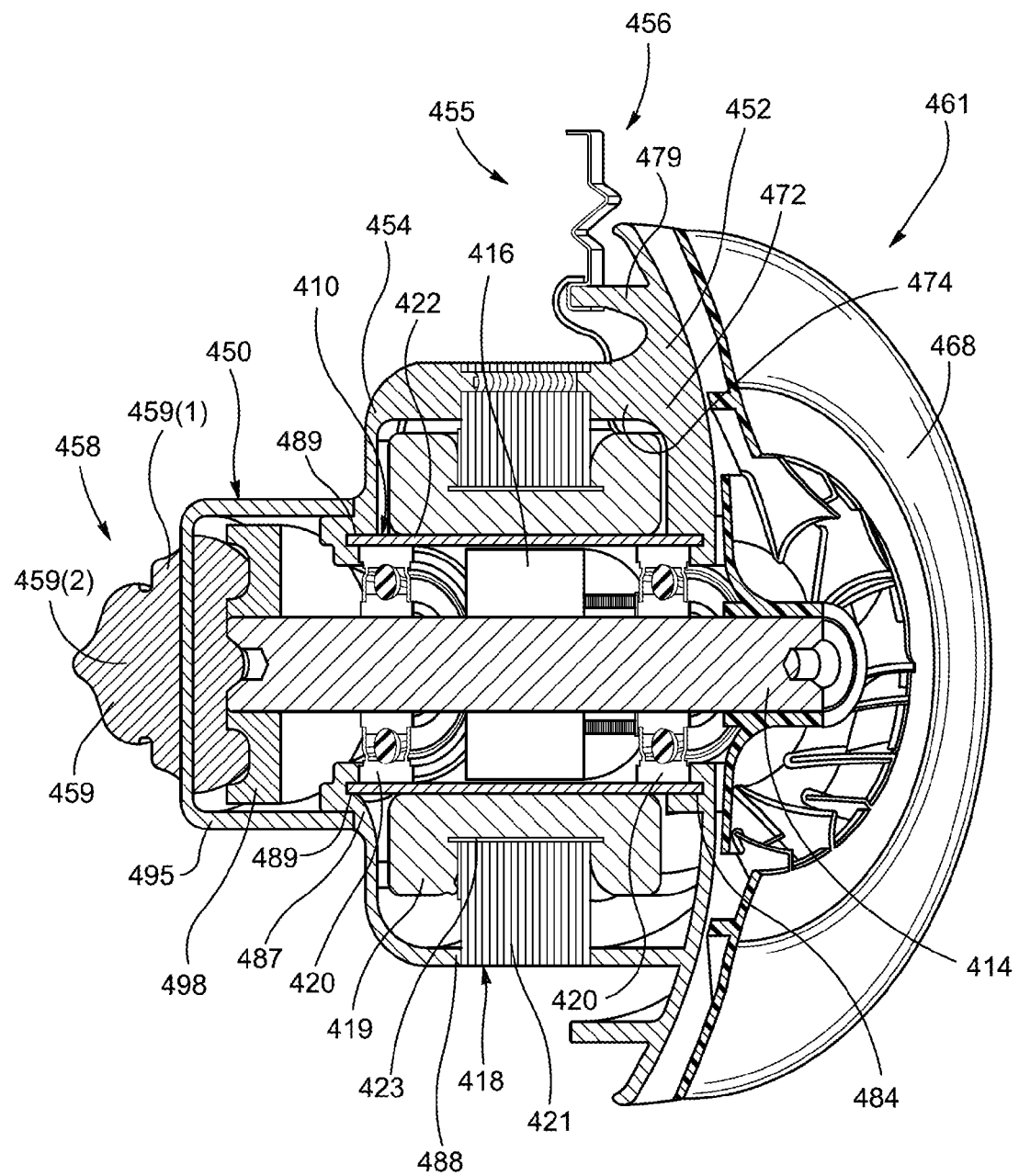
Figure 6:
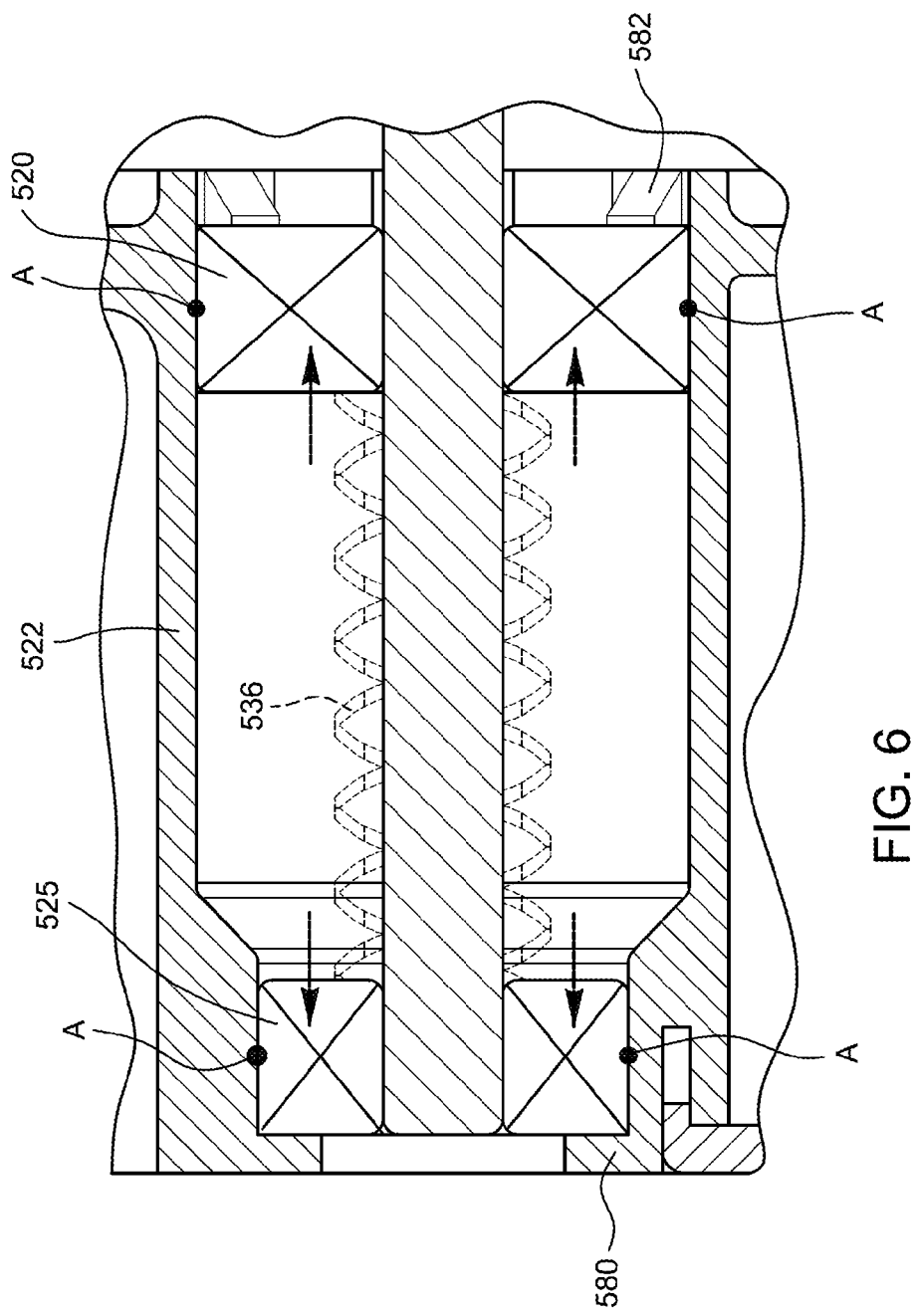
Figure 7:
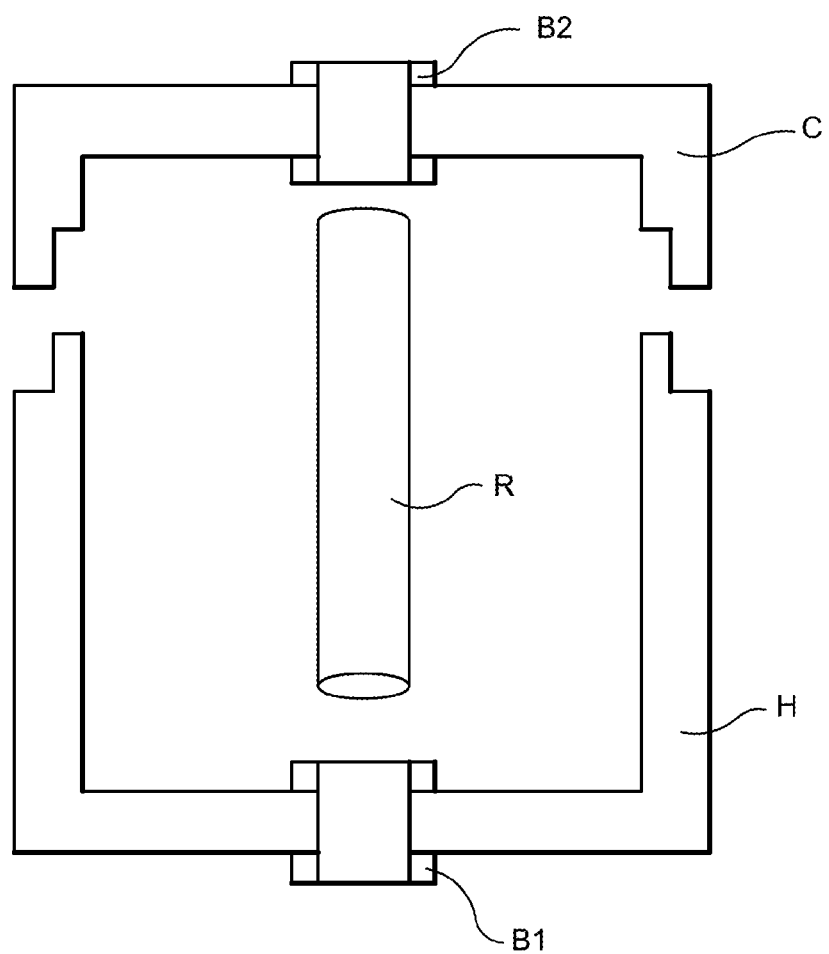
FIG. 7 is a schematic view of a prior art bearing suspension mode.
Figure 8:
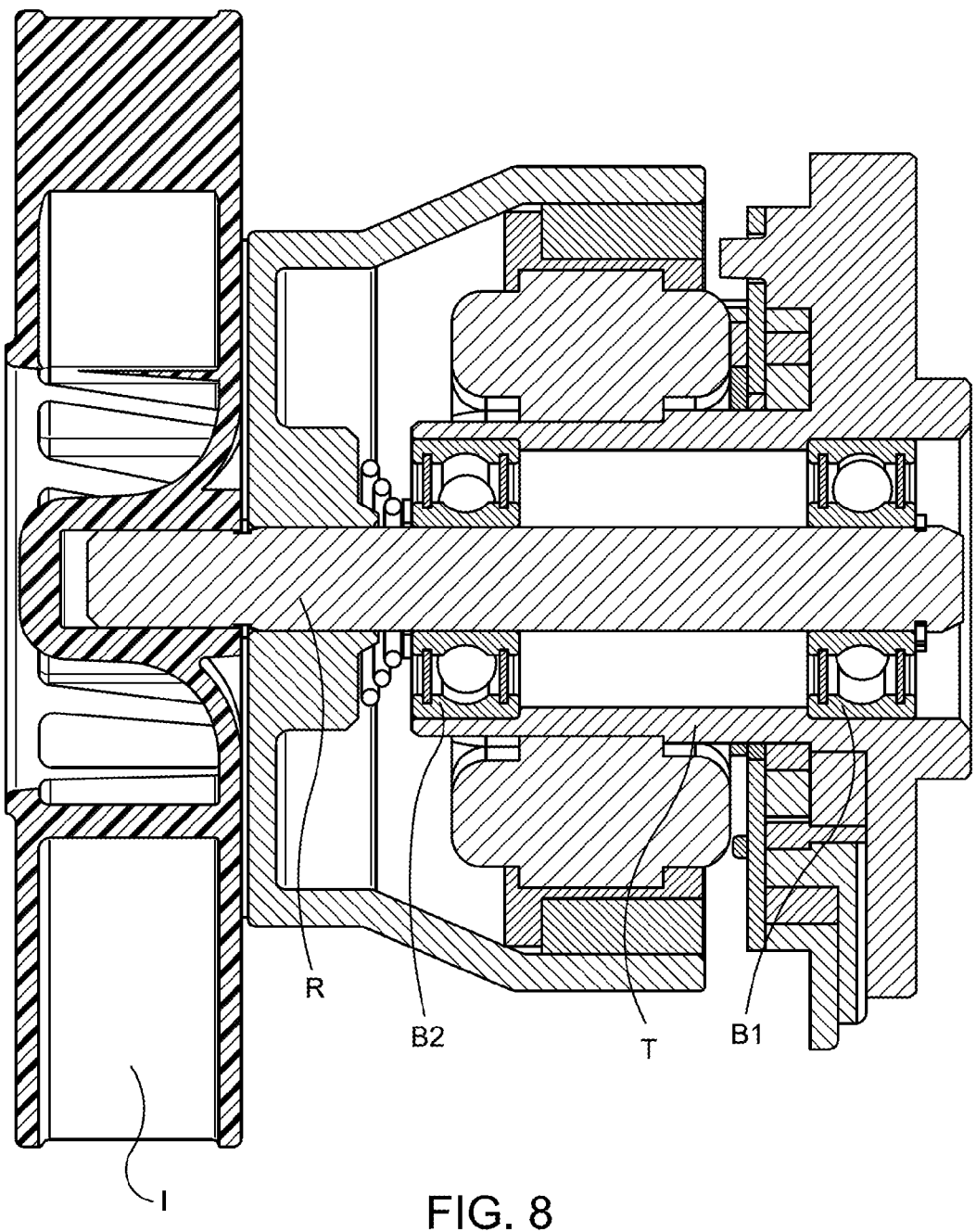
FIG. 8 is a cross-sectional view of another prior art bearing suspension mode.

Such an alternative method is illustrated in FIG. 6. In such method, a force may be applied (e.g., by spring 536 as indicated in dashed lines) to force the bearings 520, 525 against respective flanges 582, 580 and in correct alignment. Once aligned, an adhesive A, e.g., glue, or other fixing means may be applied between the bearings 520, 525 and the tube 522 to fix and retain the bearings 520, 525 in position while the force is being applied, e.g., by the spring 536. Once the bearings 520, 525 are fixedly attached, the force may be removed.

A potential problem with this alternative method is that when the motor warms up, different components (e.g., such as the rotor and the tube) will expand according to their individual thermal expansion coefficient which relates to the material used to make the components. Thus, if the rotor and the tube materials have two different thermal expansion coefficients allowing them to expand at different levels, the bearings may move or misalign causing an imbalance in the motor. In order to prevent such problems from occurring, the tube and the rotor may be made from the same material to have the same thermal expansion coefficient or the tube and the rotor may be made from two different materials with the same thermal expansion coefficient.

2.0 Motor Incorporated into PAP Device

The motor 10 may be incorporated into a PAP device or flow generator structured to generate a supply of pressurized gas to be provided to a patient for treatment, e.g., of Sleep Disordered Breathing (SDB) with Non-Invasive Positive Pressure Ventilation (NIPPVC). In an embodiment, the motor may be constructed to operate up to about 30,000 rpm and/or 8 mNm torque.

Figure 2:
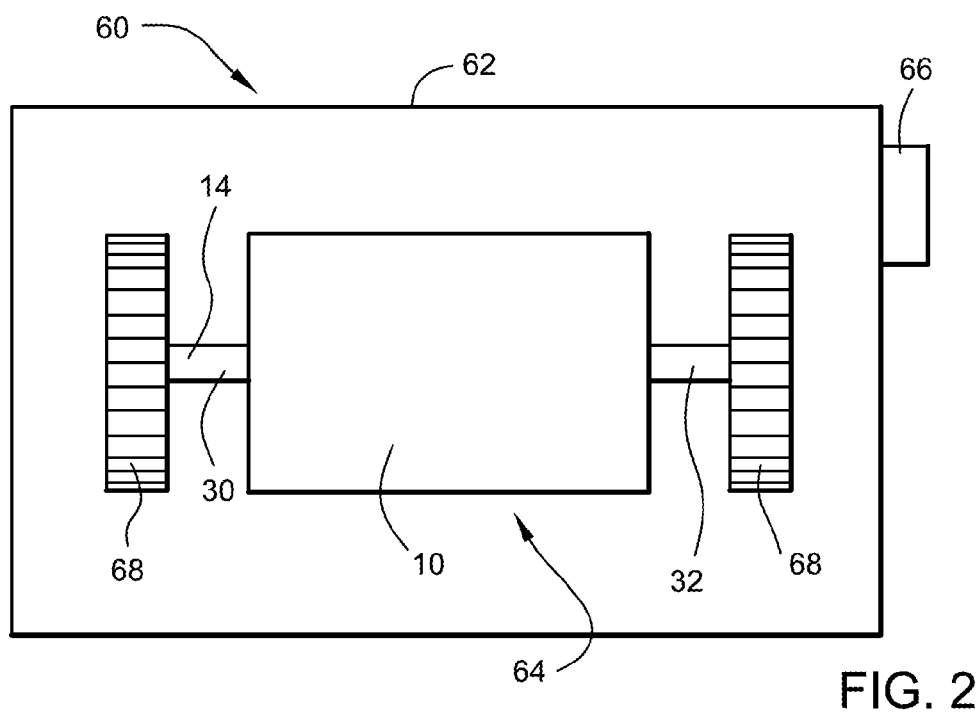
FIG. 2 is a schematic view of a PAP device including an electric motor according to an embodiment of the present invention.

For example, FIG. 2 is a schematic view of a PAP device or flow generator 60 including the motor 10. As illustrated, the PAP device 60 includes a housing 62 and a blower 64 supported within the housing 62. The blower 64 is operable to draw a supply of gas into the housing 62 through one or more intake openings (not shown, but typically provided at the bottom or side wall of the flow generator housing) and provide a pressurized flow of gas at an outlet 66. The supply of pressurized gas is delivered to the patient via an air delivery conduit that includes one end coupled to the outlet 66 of the PAP device 60 and an opposite end coupled to a mask system that comfortably engages the patient's face and provides a seal. In an embodiment, the blower is constructed to deliver pressurized gas suitable for CPAP or NIPPVC, e.g., in the range of 4-28 cmH$_2$O, at flow rates of up to 180 L/min (measured at the mask), depending on patient requirements. Also, the blower may be configured to deliver bilevel therapy or variable pressure therapy (e.g., low range of 2-6 cmH$_2$O and high range of 6-30 cmH$_2$O).

The blower 64 is supported by or within the housing 62, and includes at least one impeller 68 and the motor 10 to drive the at least one impeller 68. In the illustrated embodiment, the blower 64 has a double-ended, impeller blower construction. Specifically, the motor 10 includes the arrangement shown in FIG. 1, and each end portion 30, 32 of the rotor 14 is coupled to an impeller 68. However, the blower 64 may include a single impeller coupled to the motor 10.

The motor may incorporated into blower assemblies such as those disclosed in U.S. Pat. No. 6,910,483, U.S. Patent Publication No. 2005/0103339, and U.S. Provisional Patent Applications 60/730,875, entitled "Multiple Stage Blowers and Nested Volutes Thereof" filed Oct. 28, 2005, and 60/775,333, entitled "Blower Motor with Flexible Support Sleeve" filed Feb. 22, 2006, each of which is incorporated herein by reference in its entirety.

Also, the motor 10 may be employed in other applications.

2.1 Advantages

A PAP device or flow generator 60 including the motor arrangement of FIG. 1 has several advantages. For example, the motor arrangement of FIG. 1 provides a quieter, longer life, smaller, more reliable, and highly responsive PAP device. This provides a PAP device that is more comfortable and easier to use for the patient. Because the patients are more satisfied, therapy is easier to administer for the physician.

In addition, the PAP device 60 including the motor arrangement of FIG. 1 provides a potentially lower cost due to reduced parts count and less machining, a superior motor platform for implementing conventional rolling element bearings, a motor platform to accommodate fluid bearings, a motor platform to accommodate fluid bearings and a double-ended, impeller blower construction, and/or a motor platform to accommodate fluid bearings and a double-ended, impeller blower construction and integral volutes and/or blower housings.

3. Alternative Embodiment of Electric Motor

Figures 1, 3:
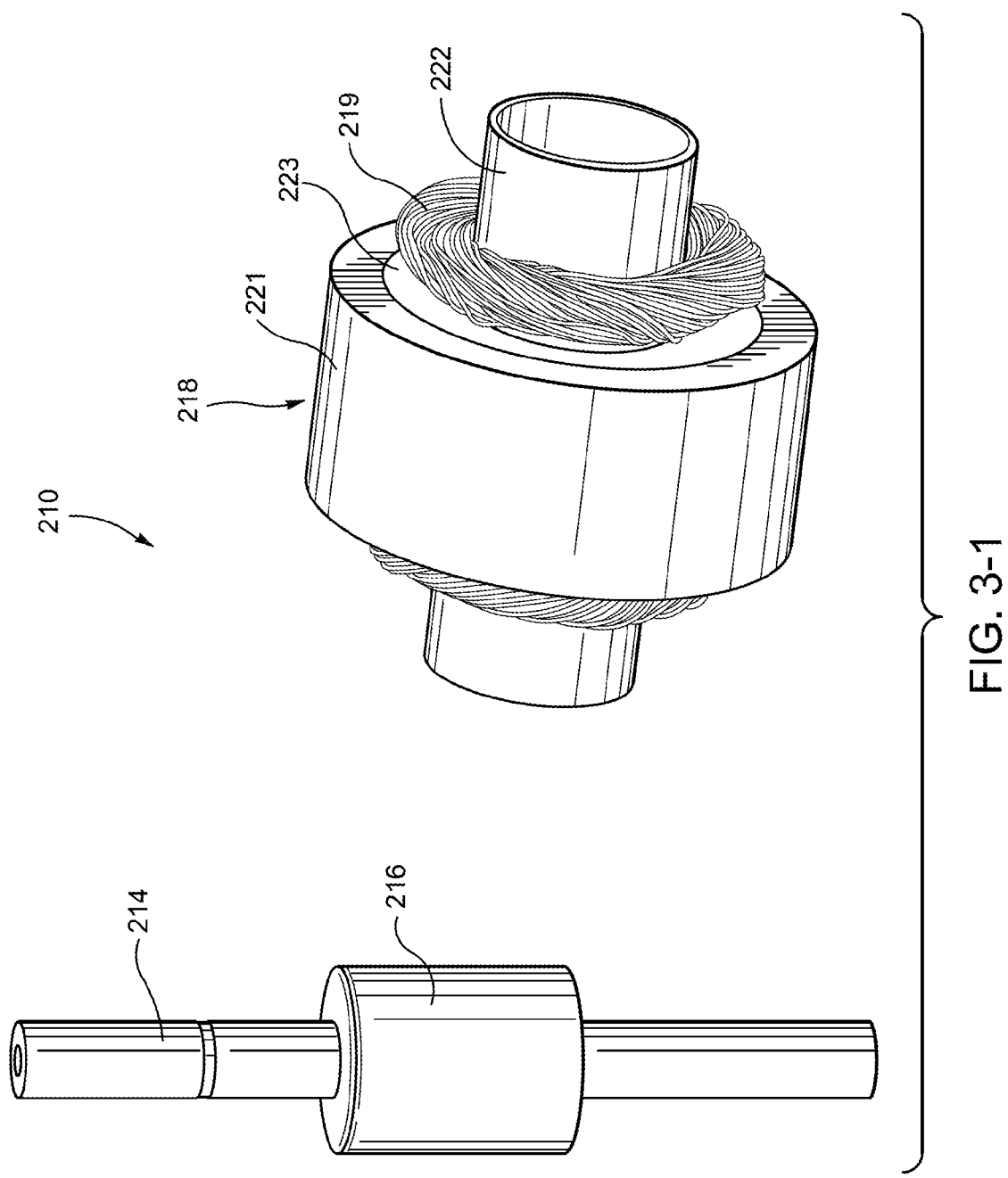
Figures 2, 3:
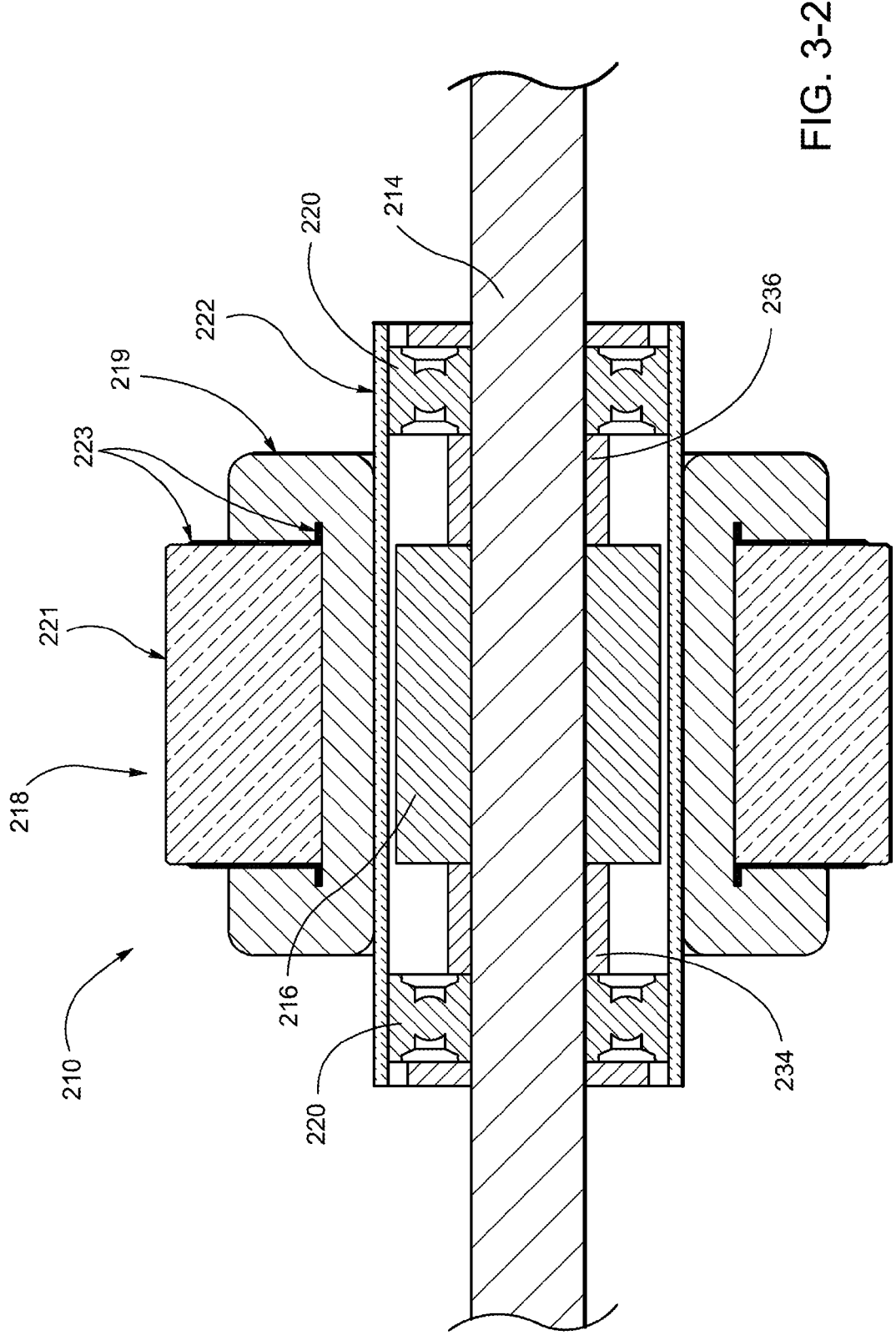

FIGS. 3-1 and 3-2 illustrate an electric motor or tube motor 210 according to another embodiment of the present invention. The tube motor 210 is substantially similar to the tube motor 10 described above, and also illustrates the motor's ability to function as a motor without the requirement of a housing or endcap.

As illustrated, the motor 210 includes a rotatable shaft or rotor 214 including a permanent magnet 216 provided thereto, a "magnetically transparent" bearing tube 222 structured to retain or house bearings 220 that rotatably support the rotor 214 within the tube 222, and a stator assembly 218 provided along an exterior surface of the tube 222 (e.g., retained on tube by friction).

In the illustrated embodiment, the stator assembly 218 includes windings 219, a stator or stator lamination stack 221 provided to the windings 219, and one or more insulators 223 provided between the windings 219 and the stack 221 to insulate the stack 221 from the windings 219. As described above, the tube 222 is "magnetically transparent", which allows the stator assembly 218 to act on the magnetic rotor 214 positioned within the tube 222 without significant loss of flux density and/or increased heat, if any.

A spacer 234 is provided between the rotor magnet 216 and one of the bearings 220, and a spring or biasing element 236 is provided between the rotor magnet 216 and the other of the bearings 220. This arrangement maintains alignment of the rotor magnet 216 with the stator assembly 218.

In the "tube motor" described herein, the housing elements are replaced by a single tube 222 that extends through the core of the stator assembly 218. The tube 22 is thin-walled (but strong) and is "magnetically transparent", which allows the bearings to be mounted within a single bore with the rotor magnet nested therebetween. The rotor's magnetic flux penetrates the wall of the tube (since the tube is "magnetically transparent") to interact with stator winding currents to produce shaft torque.

Thus, the "tube motor" is self-contained wherein the stator and rotor are supported and/or contained by the tube in a manner that allows the tube motor to function as a motor. That is, a housing or endcap is not needed to support and/or contain the stator and/or rotor, e.g., housing not needed to support motor bearings. In PAP devices, a housing and/or endcap may be provided to the tube motor to define a plenum chamber for pressurized gas.

3.1 Benefits and Features

Benefits and features of the tube motor 210 include one or more of the following:

Low cost;

Housing-less: no requirement for housing or endcap;

High performance capable;

Low inertia;

Dual shaft capable;

Tube provides excellent bore-to-bore concentricity (low noise without need for highly precise machined housing parts);

Facilitates vibration isolation;

High power efficiency (low iron loss);

Good thermal properties (especially for the stator), e.g., due to the cooling effect on the stator with pressurized gas directed around the stator. The reduced heat on the stator and bearings may increase the reliability and life of the motor. Also, heat may be passed to the pressurized gas to assist in warming the gas;

Compact construction;

Highly manufacturable;

Slotless stator (zero cogging);

Sensorless (or "sensored"—if necessary);

Sine drivable (e.g., about 1.1% THD (Total Harmonic Distortion)); and/or

Reduction or elimination in tolerances by using the tube (e.g., no tolerance may be required for the stator from the rotor/stator alignment).

It should be appreciated that the motors 10, 210 may include one or more similar advantages, benefits and/or features.

4. Alternative Embodiment of PAP Device

Figures 1, 4:
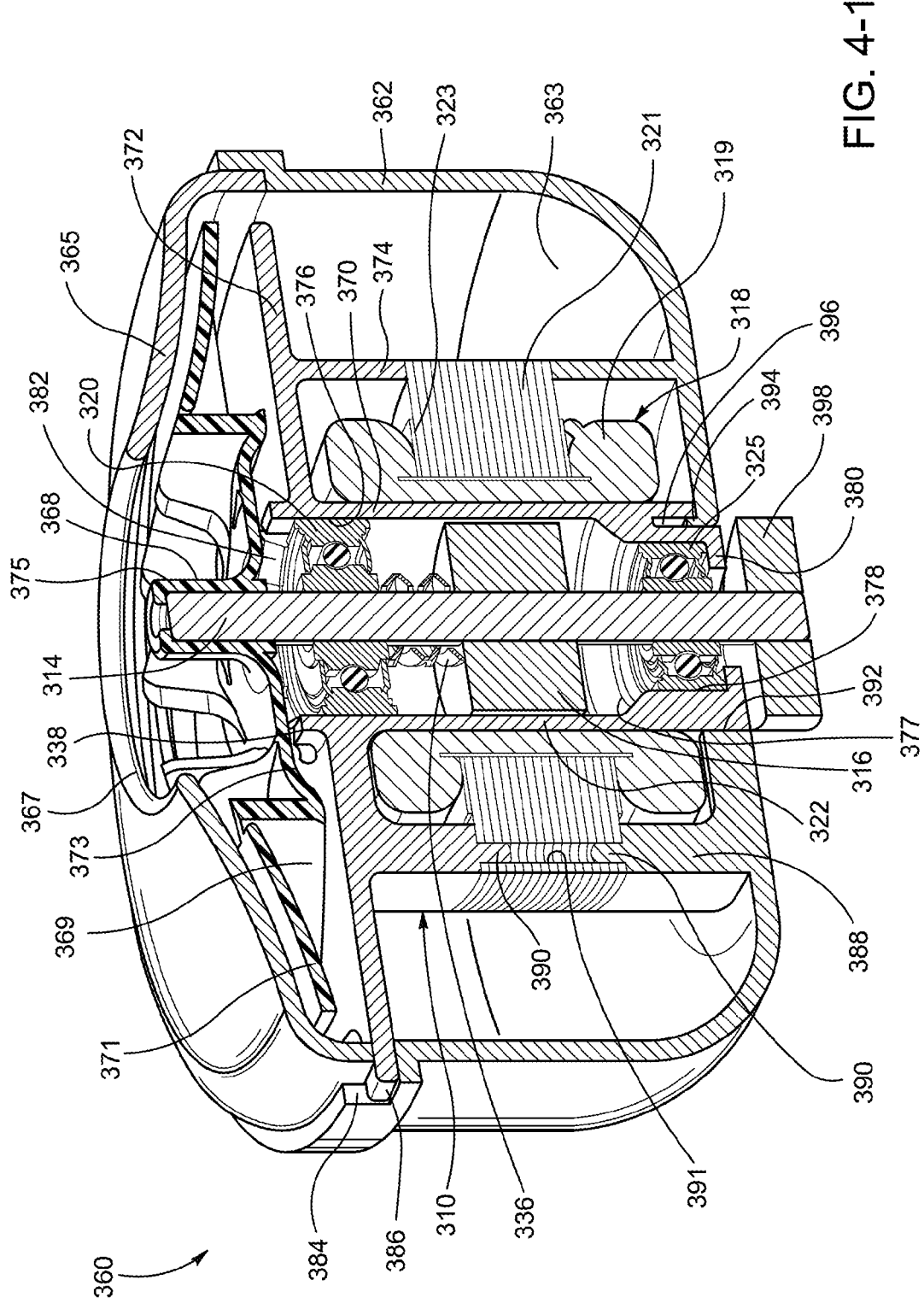
Figures 2, 4:
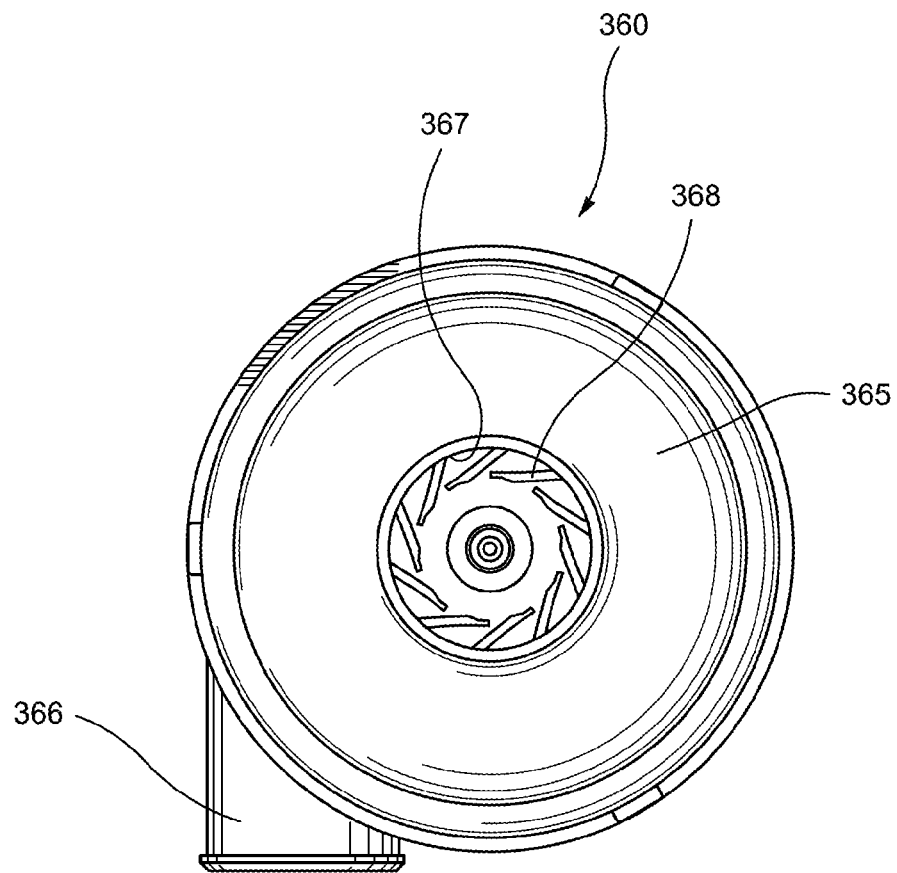
Figures 3, 4:
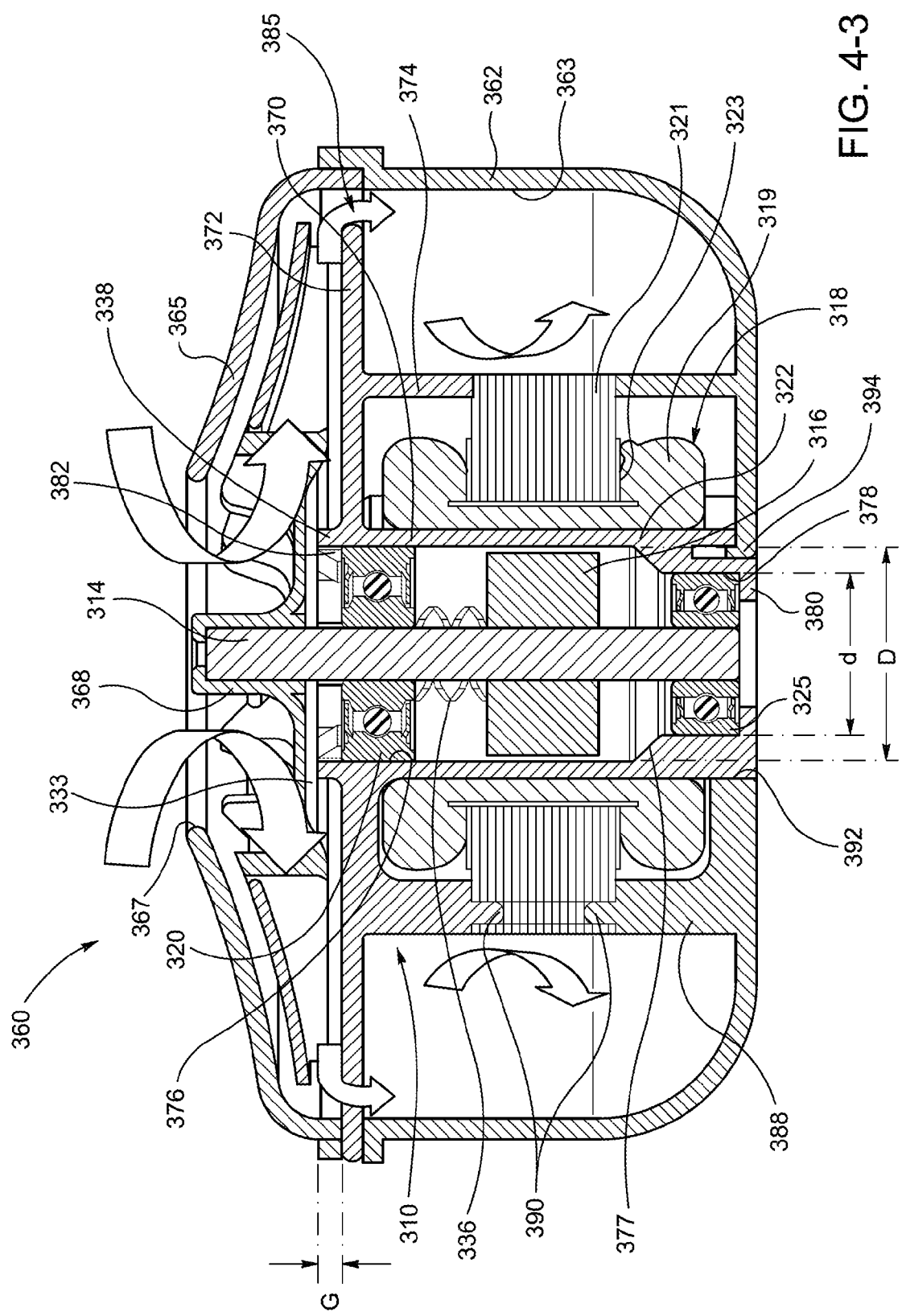

FIGS. 4-1 to 4-3 illustrate a PAP device or blower 360 according to another embodiment of the present invention. As illustrated, the PAP device 360 includes a volute or housing 362 that defines a generally spiral-shaped channel 363, a tube motor 310 including a "magnetically transparent" tube 322 support by or within the housing 362, an impeller 368 provided to the rotor 314 of the tube motor 310, and a lid or end cap 365 provided to the housing 362 to enclose the impeller 368.

As best shown in FIG. 4-2, the PAP device 360 is operable to draw a supply of gas into the housing through an inlet 367 and provide a pressurized flow of gas at an outlet 366. The PAP device 360 is generally cylindrical with the inlet 367 aligned with an axis of the PAP device and the outlet 366 structured to direct gas exiting the PAP device in a generally tangential direction.

In an embodiment, the PAP device 360 may have a diameter of about 60 mm and a height of about 30 mm, which provides a cylindrical volume of about 85 cm³. The outlet 366 may have a diameter of about 10 mm. It is to be understood that these dimensions are merely exemplary and other dimensions are possible depending on application.

4.1 Tube Motor

The tube motor 310 includes a rotatable shaft or rotor 314 including a permanent magnet 316 provided thereto, a "magnetically transparent" tube 322 structured to retain or house bearings 320, 325 that rotatably support the rotor 314 within the tube 322, and a stator assembly 318 provided along an exterior surface of the tube 322 (e.g., retained on tube by friction).

The stator assembly includes windings 319, a stator or stator lamination stack 321 (e.g., slotless or toothless) provided to the windings 319, and one or more insulators 323 provided between the windings 319 and the stack 321 to insulate the stack 321 from the windings 319. Further details of coil winding is disclosed in U.S. Provisional Application No. 60/877,373, filed Dec. 28, 2006, which is incorporated herein by reference in its entirety.

4.1.1 One-Piece Tube

The tube 322 of the tube motor 310 includes a tube portion 370, a shield 372 provided to one end of the tube portion 370, and an annular flange 374 extending from the shield 372. In the illustrated embodiment, the tube 322 is integrally molded (e.g., injection molded) as a one-piece structure. However, the tube 322 may be constructed in other suitable manners.

4.1.2 Bearing Alignment and Retention

The tube portion 370 of the tube 322 is structured to retain and align the bearings 320, 325 that rotatably support the rotor 314. In the illustrated embodiment, the tube portion 370 is structured such that mixed bearing sizes may be used.

As illustrated, the upper end of the tube portion 370 is structured to support bearing 320 and the lower end of the tube portion 370 is structured to support bearing 325 having a smaller size or diameter than bearing 320.

Specifically, the upper end of the tube portion 370 includes an annular surface 376 defining a diameter D and adapted to support bearing 320. The lower end of the tube portion 370 includes an annular surface 378 defining a smaller diameter d and adapted to support bearing 325. As illustrated, the one-piece tube portion 370 provides accurate bore-to-bore alignment which provides accurate bearing-to-bearing alignment. The upper end of the tube portion 370 also includes one or more extensions 338 structured to strengthen the upper end of the tube portion 370 supporting the bearing 320.

In an embodiment, the tube portion may be manufactured such that substantially no draft angle is provided along surfaces 376, 378 adapted to support respective bearings 320, 325. However, a draft angle may be provided along the surface between surfaces 376 and 378 to facilitate molding along the line of draw.

A sloped surface 377 may be provided between surfaces 376, 378 to guide the rotor 314 (with bearings 320, 325 provided to respective end portions) into the lower end of the tube portion 370. For example, the smaller bearing side of the rotor 314 may be inserted into or "dropped into" the tube portion 370 through the upper end of the tube portion 370. As the smaller bearing 325 approaches the lower end, the sloped surface 377 will guide the bearing 325 into engagement with surface 378 having a reduced diameter. Thus, the bearing 325 is self-guided into its operative position.

In the illustrated embodiment, the lower end of the tube portion 370 includes a flange 380 that provides a stop or support for the bearing 325 at the lower end. Also, the upper end of the tube portion 370 includes one or more tapered flange portions 382 adapted to engage the bearing 320, and hence retain the rotor within the tube portion 370.

The tapered flange portions 382 provide snap-in bearing retention. That is, the tapered flange portions 382 may be resiliently deflected upon rotor assembly to allow the bearing 320 to snap into the tube portion 370, but prevent removal of the bearing 320 (and hence the rotor) from the tube portion 370 once assembled.

A spring or biasing element 336 may be provided between the bearing 320 and the rotor magnet 316 to maintain alignment of the rotor magnet 316 with the stator assembly 318.

4.1.3 Shield

The shield 372 of the tube 322 forms an upper wall or cutoff for the channel 363 that directs pressurized gas to the outlet 366. In the illustrated embodiment, the shield 372 is in the form of a circular disk that is provided to (e.g., integrally formed in one-piece) an end of the tube portion 370 adjacent the impeller 368.

In the illustrated embodiment, the outer edge of the shield 372 substantially aligns with or extends radially beyond the outer edge of the impeller 368. The shield 372 provides a narrow annular gap 385 (e.g., about 1 mm) between its outer edge and the wall of the housing 362, which is sufficient to direct gas into the channel 363 leading to the outlet 366.

4.2 Tube Motor and Housing Engagement

The tube motor 310 and the housing 362 provide complementary structural elements that are adapted to support, align, and/or contain the tube motor 310 within the housing 362.

In the illustrated embodiment, the housing 362 includes one or more slots 384 in an upper portion of the housing wall that is adapted to receive respective tabs 386 provided along the outer edge of the shield 372 (e.g., see FIG. 4-1). In an embodiment, the shield 372 includes three tabs 386 that are received in respective slots 384 of the housing 362. However, any suitable number of slots/tabs may be provided.

The housing 362 and tube 322 cooperate to support and maintain the stator assembly 318 in an operative position. As illustrated in FIGS. 4-1 and 4-3, the annular flange 374 of the tube 322 is structured to enclose an upper portion of the windings 319 and engage an upper side of the stack 321. Similarly, the bottom wall of the housing 362 includes an annular flange 388 that is structured to enclose a lower portion of the windings 319 and engage a lower side of the stack 321. Thus, the annular flanges 374, 388 cooperate to enclose and sandwich the stator assembly 318 between the housing 362 and the tube 322.

Also, each flange 374, 388 includes one or more anchoring protrusions 390 (also referred to as anchoring pips or locating pins) that are adapted to engage within corresponding holes 391 provided through the stack 321. This arrangement self-adheres and/or aligns the housing 362 and the tube 322 to the stack 321. In the illustrated embodiment, exterior surfaces of the flanges 374, 388 are substantially flush with an exterior surface of the stack 321.

In addition, the bottom wall of the housing 362 includes an opening 392 adapted to receive the lower end of the tube portion 370 of the tube 322. One or more tabs 394 may be provided along the edge of the opening 392 that are adapted to engage within respective openings 396 provided in the lower end of the tube portion 370.

In an embodiment, the above-described complementary structural elements provided to the tube motor 310 and the housing 362 may provide snap-fit retention.

4.3 Impeller

In the illustrated embodiment, the PAP device 360 includes a single impeller 368. As illustrated, the impeller 368 includes a plurality of continuously curved or straight blades 369 sandwiched between a pair of disk-like shrouds 371, 373. The smaller shroud 373 incorporates the hub or bushing 375 that is adapted to receive an end portion of the rotor 314. Further details of impellers are disclosed in PCT Application No. PCT/AU2006/001617, filed Oct. 27, 2006, which is incorporated herein by reference in its entirety.

This arrangement provides a low cost and low inertia alternating shroud impeller. In an embodiment, a gap G (e.g., see FIG. 4-3) may be controlled by a press-to-shim technique. For example, a shim 333 may be provided along the upper end of the tube 322 that is adapted to engage the lower end of the hub 375 of the impeller 368 (as the hub 375 is mounted to the rotor 314) and hence control the size of the gap G.

In an embodiment, the impeller 368 may have a diameter of about 50 mm. It is to be understood that this dimension is merely exemplary and other dimensions are possible depending on application.

4.4 Optional Balance Ring

As shown in FIG. 4-1, a balance ring 398 may be optionally provided to an opposite end portion of the rotor 314 (opposite the end portion supporting the impeller 368).

This arrangement may facilitate single-plane or two-plane balancing of the tube motor 310.

4.5 Fluid Flow Path

As best shown in FIG. 4-3, gas enters the PAP device at the inlet 367 and passes into the impeller 368 where it is accelerated tangentially and directed radially outward. The gap 385 between the outer edge of the shield 372 and the wall of the housing 362 allows gas to pass into the channel 363 and down around the sides of the tube motor 310. Gas passes around the channel 363 and the sides of the tube motor 310 flowing in a spiral manner with towards the outlet 366.

4.5.1 Stator Cooling

In the illustrated embodiment, the exterior surface of the stack 321 of the stator assembly 318 is exposed to the channel 363 of the housing 362 and hence is exposed to the gas passing through the channel 363. This arrangement allows forced-convection cooling of the stack 321 as gas flows through the channel 363 in use.

4.6 Simple Construction and Low Cost

The PAP device 360 includes a relatively basic construction with a single impeller to provide relatively basic CPAP and/or SnorePAP treatment.

In addition, the PAP device 360 provides four plastic molded (e.g., injection-molded) parts, i.e., the housing 362, the tube 322, the impeller 368, and the end cap 365. These molded parts (along with the rotor 314, stator assembly 318, bearings 320, 325, and spring 336) provide an arrangement with relatively low component and assembly costs.

5. PAP Device with Flexible Core

FIGS. 5-1 to 5-6 illustrate a PAP device or blower 460 (e.g., to provide CPAP through BiLevel NIV treatment) according to another embodiment of the present invention. In this embodiment, the PAP device 460 includes a housing 462 and a core 461 supported within the housing 462 by a vibration isolation system 455. As described in greater detail below, the vibration isolation system 455 supports the core 461 in a flexible, vibration-isolated manner with respect to the housing 462 so that the core 461 is substantially isolated from the housing 463. Thus, vibrations and/or other movement generated by the core 461 in use are substantially isolated from the housing 462.

5.1 Core

In the illustrated embodiment, the core 461 includes a tube motor 410 including a "magnetically transparent" tube 422, a core housing 450 structured to substantially enclose the tube motor 410, an impeller 468 provided to one end portion of the rotor 414 of the tube motor 410, and a balance ring 498 provided to an opposite end portion of the rotor 414.

5.1.1 Tube Motor

As described above, the tube motor 410 includes a rotatable shaft or rotor 414 including a permanent magnet 416 provided thereto, a "magnetically transparent" tube 422 structured to retain or house bearings 420 that rotatably support the rotor 414 within the tube 422, and a stator assembly 418 provided along an exterior surface of the tube 422 (e.g., retained on tube by friction).

The stator assembly 418 includes windings 419, a stator or stator lamination stack 421 (e.g., slotless or toothless) provided to the windings 419, and one or more insulators 423 provided between the windings 419 and the stack 421 to insulate the stack 421 from the windings 419.

A spring or biasing element 436 may be provided between one of the bearings 420 and the rotor magnet 416 to maintain alignment of the rotor magnet 416 with the stator assembly 418.

5.1.2 Core Housing

In the illustrated embodiment, the core housing 450 includes a first housing part 452 provided to one end of the tube 422 and a second housing part 454 provided to the opposite end of the tube 422.

As illustrated, the first housing part 452 includes a shield 472 that forms an upper wall or cutoff for the housing channel 463. An inner annular flange 474 and an outer annular flange 479 extend from the shield 472. In the illustrated embodiment, the shield 472 and impeller 468 have a tapered or sloped configuration along its radial length. However, other suitable configurations of the shield and impeller are possible.

As described above, the shield 472 provides a narrow annular gap 485 between its outer edge and the housing 462, which is sufficient to direct gas into the housing channel 463.

The shield 472 includes an opening that allows one end portion of the rotor 414 to pass therethrough. The edge of the opening includes an annular slot 484 that is adapted to receive one end of the tube 422.

Also, the inner annular flange 474 is structured to enclose an upper portion of the windings 419 and engage an upper side of the stack 421. The inner annular flange 474 includes one or more anchoring protrusions 490 that are adapted to engage within corresponding holes 491 provided through the stack 421.

The second housing part 454 includes a main wall 487 and an annular flange 488 extending from the main wall 487. The main wall 487 includes an opening that allows the opposite end portion of the rotor 414 to pass therethrough. The edge of the opening includes an annular slot 489 that is adapted to receive the opposite end of the tube 422.

Also, the annular flange 488 is structured to enclose a lower portion of the windings 419 and engage a lower side of the stack 421. The annular flange 488 includes one or more anchoring protrusions 493 that are adapted to engage within corresponding holes 491 provided through the stack 421.

Thus, the flanges 474, 488 cooperate to enclose and sandwich the stator assembly 418. In the illustrated embodiment, exterior surfaces of the flanges 474, 488 are substantially flush with an exterior surface of the stack 421, i.e., exterior surface of stack exposed. As described above, this arrangement allows forced-convection cooling of the stack 421 as gas flows through the housing channel 463 in use.

The core housing 450 also includes a cap 495 provided to the second housing part 454 and adapted to enclose the balance ring 498 at one end portion of the rotor 414.

In an alternative embodiment, one or portions of the core housing 450 may be integrally formed in one piece with the tube 422, e.g., similar to tube 322 described above.

5.2 Housing

The housing 462 includes a main body 481 that provides an outer wall for the housing channel 463 and a lid or end cap 465 provided to the main body 481 to enclose the core 461.

As best shown in FIGS. 5-1 and 5-4, the PAP device 460 is operable to draw a supply of gas into the housing through an inlet 467 and provide a pressurized flow of gas at an outlet 466. The PAP device 460 is generally cylindrical with the inlet 467 aligned with an axis of the PAP device and the outlet 466 structured to direct gas exiting the PAP device in a generally tangential direction.

5.3 Vibration Isolation System

The vibration isolation system 455 includes a front suspension 456 (or front vibration isolator) to support a front portion of the core 461 and a rear suspension 458 (or rear vibration isolator) to support a rear portion of the core 461. The front and rear suspension 456, 458 together support the core 461 in a flexible, vibration-isolated manner with respect to the housing 462.

5.3.1 Front Suspension

The front suspension 456 includes a plurality of biasing elements 457, e.g., flat springs. As best shown in FIG. 5-3, each biasing element 457 includes one end portion 457(1) provided to the outer annular flange 479 of the shield 472 of the core 461, an opposite end portion 457(2) provided to the main body 481 of the housing 462, and an intermediate portion 457(3) that provides a flexible structure to isolate the core 461 from the housing 462.

In the illustrated embodiment, the one end portion 457(1) includes a bent configuration adapted to receive the free end of the flange 479. The opposite end portion 457(2) includes a bent configuration adapted to engage within a slot 483 provided to the main body 481. The intermediate portion 457(3) is bent into a concertina or bellow-like configuration to provide a flexible structure.

In use, the biasing elements 457 support the front portion of the core 461 within the housing 462 while isolating the core 461 from the housing 462, e.g., vibration isolated.

In addition, wire W from the windings 419 may be coupled to one or more of the biasing elements 457, e.g., wire W connected to the end portion 457(1). This allows the biasing elements 457 (e.g., flat springs formed of metal) to conduct current from an external source to the windings 419. For example, FIGS. 5-1 and 5-2 illustrate external source S that may be coupled to end portion 457(2) to conduct current through the biasing element 457 and to wire W from windings 419.

5.3.2 Rear Suspension

The rear suspension 458 is in the form of a resiliently flexible nipple 459 (e.g., formed of a silicone material) having one end 459(1) provided to the cap 495 of the core housing 450 and an opposite end 459(2) provided to the main body 481 of the housing 462.

In the illustrated embodiment, the end 459(2) includes an annular recess 497 adapted to receive the edge of an opening 499 provided in the lower wall of the main body 481.

In use, the resiliently flexible nipple 459 support the rear portion of the core 461 within the housing 462 while isolating the core 461 from the housing 462, e.g., vibration isolated.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. A brushless DC motor, comprising:
a rotor having a magnet;
a pair of bearings configured to rotatably support the rotor;
a stator assembly configured to control movement of the rotor; and
a tube provided between the rotor and the stator assembly,
wherein the tube includes a one-piece structure, the tube including an interior surface configured to retain and align the pair of bearings that rotatably support the rotor and magnet within an interior of the tube, and the stator assembly is provided along an exterior surface of the tube,
wherein the tube includes at least a portion that is sufficiently magnetically transparent configured to allow a magnetic field to pass between the magnet and the stator assembly,
wherein the pair of bearings includes a first bearing and a second bearing that has a smaller size than the first bearing,
wherein a first end of the tube includes a first portion of the interior surface configured to support the first bearing and an opposite, second end of the tube includes a second portion of the interior surface configured to support the second bearing having the smaller size, and
wherein the tube is configured such both the first bearing and the second bearing are inserted into the interior and into engagement with the interior surface through the first end of the tube.

2. The motor according to claim 1, wherein the tube is constructed of a substantially non-electrically conductive and/or non-magnetic material.

3. The motor according to claim 1, wherein the tube is constructed of a substantially thermally conductive material.

4. The motor according to claim 1, wherein the tube includes structural and/or material properties that are sufficiently magnetically transparent to allow a magnetic field to pass between the magnet and the stator assembly.

5. The motor according to claim 4, wherein the tube is sufficiently perforated to allow a magnetic field to pass through it.

6. The motor according to claim 1, wherein the bearings include rolling element bearings, fluid bearings, and/or sleeve bearings.

7. The motor according to claim 1, wherein the tube is constructed of ceramics, glass, polymers, filled (non-conductive) polymers, or reinforced polymers.

8. The motor according to claim 7, wherein the tube is constructed of stabilized zirconia.

9. The motor according to claim 7, wherein the tube is constructed of fiberglass, carbon, or boron.

10. The motor according to claim 1, the interior surface is continuous and non-jointed from the first portion to the second portion, and wherein the interior surface includes a sloped portion between the first portion and the second portion to guide the second bearing into the second portion.

11. The motor according to claim 1, further comprising a shield provided to one end of the tube, wherein the shield and the tube comprise the one-piece structure, and wherein the shield includes an outer edge that extends radially beyond an outer edge of the stator assembly.

12. A PAP device for generating a supply of pressurized gas to be provided to a patient for treatment, the PAP device comprising:
a housing; and
a blower provided to the housing, the blower operable to provide a pressurized flow of gas at an outlet,
wherein the blower includes at least one impeller and the motor according to claim 1 to drive the at least one impeller.

13. The PAP device according to claim 12, wherein the at least one impeller is coupled to an end portion of the rotor, the end portion provided exterior to the tube.

14. The motor according to claim 1, wherein the pair of bearings are provided to the rotor to form a unit that as a whole is subsequently engaged with the tube.

15. The motor according to claim 1, wherein the second end of the tube includes a flange that provides a stop or support for the second bearing at the second end.

16. The motor according to claim 15, wherein the flange is configured to prevent insertion of the first bearing and the second bearing into the interior of the tube through the second end of the tube.

17. A brushless DC motor, comprising:
a rotor;
a magnet provided to the rotor;
a pair of bearings configured to rotatably support the rotor;
a stator assembly that at least partly surrounds the rotor and magnet thereof, the stator assembly configured to control movement of the rotor; and
a bearing tube having an exterior surface and an interior surface that forms a tube interior,
wherein the stator assembly is provided along the exterior surface of the tube and the pair of bearings are provided along the interior surface of the tube to support the rotor and magnet within the tube interior,
wherein the pair of bearings includes a first bearing and a second bearing that has a smaller size than the first bearing,
wherein a first end of the bearing tube includes a first portion of the interior surface configured to support the first bearing and an opposite, second end of the bearing tube includes a second portion of the interior surface configured to support the second bearing having the smaller size, and
wherein the interior surface is continuous and non-jointed from the first portion to the second portion, and wherein the interior surface includes a sloped portion between the first portion and the second portion to guide the second bearing into the second portion.

18. The motor according to claim 17, wherein the bearings include rolling element bearings, fluid bearings, and/or sleeve bearings.

19. The motor according to claim 17, wherein the tube has at least a portion that is sufficiently magnetically transparent to allow a magnetic field to pass between the magnet and the stator assembly.

20. The motor according to claim 17, wherein the bearing tube is constructed of a substantially non-electrically conductive and/or non-magnetic material.

21. The motor according to claim 17, wherein the tube is constructed of a thermally conductive material.

22. The motor according to claim 17, wherein the tube includes structural and/or material properties that are sufficiently magnetically transparent to allow a magnetic field to pass between the magnet and the stator assembly.

23. The motor according to claim 22, wherein the tube is sufficiently perforated to allow a magnetic field to pass through it.

24. The motor according to claim 17, wherein the tube is constructed of ceramics, glass, polymers, filled (non-conductive) polymers, or reinforced polymers.

25. The motor according to claim 19, wherein the tube is constructed of stabilized zirconia.

* * * * *